United States Patent
Chadeayne

(10) Patent No.: US 11,974,984 B2
(45) Date of Patent: May 7, 2024

(54) COMPOSITIONS AND METHODS COMPRISING A COMBINATION OF SEROTONERGIC DRUGS

(71) Applicant: CAAMTECH, LLC, Issaquah, WA (US)

(72) Inventor: Andrew R. Chadeayne, Issaquah, WA (US)

(73) Assignee: CAAMTECH, INC., Issaquah, WA (US)

(*) Notice: Subject to any disclaimer, the term of this patent is extended or adjusted under 35 U.S.C. 154(b) by 102 days.

(21) Appl. No.: 17/095,430

(22) Filed: Nov. 11, 2020

(65) Prior Publication Data

US 2021/0085671 A1    Mar. 25, 2021

Related U.S. Application Data

(63) Continuation-in-part of application No. 15/893,562, filed on Feb. 9, 2018, now Pat. No. 10,933,073.

(60) Provisional application No. 62/613,360, filed on Jan. 3, 2018, provisional application No. 62/609,115, filed on Dec. 21, 2017, provisional application No. 62/598,767, filed on Dec. 14, 2017, provisional application No. 62/595,321, filed on Dec. 6, 2017, provisional application No. 62/595,336, filed on Dec. 6, 2017, provisional application No. 62/593,021, filed on Nov. 30, 2017, provisional application No. 62/592,320, filed on Nov. 29, 2017, provisional application No. 62/592,307, filed on Nov. 29, 2017, provisional application No. 62/587,395, filed on Nov. 16, 2017, provisional application No. 62/587,419, filed on Nov. 16, 2017, provisional application No. 62/587,410, filed on Nov. 16, 2017, provisional application No. 62/587,431, filed on Nov. 16, 2017, provisional application No. 62/457,123, filed on Feb. 9, 2017.

(51) Int. Cl.
*A61K 31/4045* (2006.01)
*A61K 31/36* (2006.01)
*A61K 31/48* (2006.01)

(52) U.S. Cl.
CPC .......... *A61K 31/4045* (2013.01); *A61K 31/36* (2013.01); *A61K 31/48* (2013.01)

(58) Field of Classification Search
CPC ..... A61K 31/4045; A61K 31/36; A61K 31/48
See application file for complete search history.

(56) References Cited

U.S. PATENT DOCUMENTS

| | | | |
|---|---|---|---|
| 3,192,111 A | 6/1965 | Hofmann et al. | |
| 6,303,181 B1 | 10/2001 | Terranova et al. | |
| 6,306,181 B1 | 10/2001 | Terranova et al. | |
| 8,859,579 B2 | 10/2014 | Sewell | |
| 10,933,073 B2 | 3/2021 | Chadeayne | |
| 2004/0034106 A1 | 2/2004 | Read et al. | |
| 2005/0137255 A1* | 6/2005 | Petersen ............ | C07D 307/87 549/467 |
| 2008/0293695 A1 | 11/2008 | Bristol | |
| 2011/0038958 A1 | 2/2011 | Kikuchi et al. | |
| 2014/0243405 A1 | 8/2014 | Whalley et al. | |
| 2015/0320814 A1 | 11/2015 | Patel et al. | |
| 2016/0158298 A1 | 6/2016 | Kolsky | |
| 2016/0250270 A1 | 9/2016 | Wendshuh et al. | |
| 2016/0279073 A1 | 9/2016 | Donsky et al. | |
| 2018/0021326 A1 | 1/2018 | Stamets | |
| 2019/0105313 A1 | 4/2019 | Stamets | |
| 2019/0142851 A1 | 5/2019 | Chadeayne | |
| 2019/0192498 A1 | 6/2019 | Stamets | |
| 2019/0350949 A1 | 11/2019 | Kucuksen et al. | |
| 2020/0375967 A1 | 12/2020 | Stamets | |
| 2021/0069170 A1 | 3/2021 | Stamets | |

FOREIGN PATENT DOCUMENTS

| | | | | |
|---|---|---|---|---|
| GB | 2571696 B | * | 5/2020 | .......... A61K 31/661 |
| WO | 2015127556 A1 | | 9/2015 | |
| WO | 2018135943 A1 | | 7/2018 | |

OTHER PUBLICATIONS

Carhart-Harris et al. Lancet Psychiatry, 2016, vol. 3, pp. 619-627 (Year: 2016).*
Carhart-Harris et al. Neuropsychopharmacology, 2017, vol. 42, pp. 2105-2113 (Published Online May 17, 2017) (Year: 2017).*
Shirota et al. J. Nat. Prod., 2003, vol. 66, pp. 885-887 (Year: 2003).*
Chen et al., "Chemistry of Chinese Edible and Medicinal Fungi," Shanghai Science and Technology Press, 2016, ISBN: 978-7-5439-6915-5.
Dörner et al., "Genetic survey on Psilocybe natural products," Wiley-VCH, pp. 1-8, 2022.
Du Xiu-ju et al., Mushroom Toxins and Present Research of Its Utilization, Journal of Anhul Agri Sci, 2010,38 (13) : 7172-7174.
Health Canada, Notice to Stakeholders: Considerations regarding the proposed use of psilocybin mushrooms in clinical trials, or as a drug accessed through the Special Access Program (SAP), Government of Canada, May 6, 2022.
Stamets at al. Psilocybin Mushrooms of the World: An Identification Guide. First Edition. Berkeley, Calif: Ten Speed Press; 1996.
Shroomery, Re: LSA and Shrooms [Re: MycoKris], Sep. 5, 2006, https://www.shroomery.org/forums/showflat.php/Number/6033473#6033473.

(Continued)

*Primary Examiner* — James D. Anderson
(74) *Attorney, Agent, or Firm* — RAPHAEL BELLUM PLLC

(57) ABSTRACT

This disclosure pertains to new compositions and methods comprising a first serotonergic drug and a second serotonergic drug. In one embodiment, the compositions disclosed herein are used for a method of regulating a neurotransmitter receptor, e.g., a serotonin receptor. In one embodiment, the compositions disclosed herein comprise purified compounds, e.g., a purified psilocybin derivative, a purified cannabinoid, a purified terpene, a purified tryptamine, purified LSD, and/or purified MDMA.

12 Claims, No Drawings

(56) References Cited

OTHER PUBLICATIONS

Shelton et al, Olanzapine/fluoxetine combination for treatment-resistant depression: a controlled study of SSRI and nortriptyline resistance, vol. 66(10) pp. 1289-1297, Oct. 2005, Journal of Clinical Psychiatry.

Sessa et al, Underground MDMA-, LSD- and 2-CB-assisted individual and group psychotherapy in Zurich: Outcomes, implications and commentary, vol. 2 pp. 1-8, 2015, Drug Science, Policy and Law.

Leeann, Personal Story: Iboga and Psilocybin Mushrooms Saved Me on the Brink of Suicide, Dec. 3, 2015, https://web.archive.org/web/20151203193708/https://reset.me/personal-story/personal-story-iboga-and-magic-mushrooms-saved-me-on-the-brink-of-suicide/.

Szegedi et al, Combination treatment with clomipramine and fluvoxamine: drug monitoring, safety, and tolerability data, vol. 57(6) pp. 257-264, Jun. 1996, Journal of Clinical Psychiatry.

Alper et al, The ibogaine medical subculture, vol. 115(1) pp. 9-24, 2008, Journal of Ethnopharmacology.

Gilman, "Compass Pathways Offers More Proof SSRI Drugs Do No Impede Psilocybin's Therapeutic Effect," Psychedelic Spotlight, Dec. 13, 2021, https://psychedelicspotlight.com/compass-pathways-study-ssri-drugs-psilocybin-therapeutic-effect/.

International Search Report in International Application No. PCT/US2018/017710, dated Jul. 9, 2018.

International Preliminary Report on Patentability in International Application No. PCT/US2018/017710, dated Aug. 22, 2019.

Leung et al. 'Baeocystin and norbaeocystin: New Analogs of psilocybin from Psilocybe baeocystis', Journal of Pharmaceutical Sciences, Oct. 1968, vol. 57, pp. 1667-1671; p. 1667, p. 1668.

Daly et al. 'The Chemorelease of Norepinephrine from Mouse Hearts, Structure-Activity Relationships. I. Sympathomimetic and Related Amines', Journal of Medicinal Chemistry, May 1966, vol. 9, pp. 273-280; p. 273, p. 279.

Glennon 'Central serotonin receptors as targets for drug research', Journal of Medicinal Chemistry, Jan. 1987, vol. 30, pp. 1-12; p. 1, p. 6, p. 7.

Jensen et al. 'Aeruginascin, a Trimethylammonium Analogue of Psilocybin from the Hallucinogenic Mushroom Inocybe aeruginascens', Planta Medica, Apr. 28, 2006 (Apr. 28, 2006), vol. 72, pp. 1-3; Abstract.

Pubmed Compound Summary for CID 17868117, '2-(4-Hydroxy-1H-indol-3-yl)ethyl-trimethylazanium', U.S. National Library of Medicine, Dec. 4, 2007 (Dec. 4, 2007), p. 1-12 (https://pubchem.ncbi.nim.nih.gov/compound/17868117); p. 4.

Niels Jensen, "Tryptamines as Ligands and Modulators of the Serotonin 5-HT 2A Receptor and the Isolation of Aeruginascin from the Hallucinogenic Mushroom *Inocybe aeruginascens*", Dissertation zur Erlanggun des Doktogrades der Mathermatisch-Naturwissenschaftlichen Fakultaeten der Georg-August-Universistaet zu Goettingen, Hamburg, 2004.

El-Alfy et al., Pharmacal. Biochem. Behav., 2010, vol. 95, No. 4, apges 434-442 (Year: 201 0).

Vollenweider et al., Nature Reviews Neuroscience, 2010, vol. 11, No. 9, pp. 642-651 (Year: 201 0).

Maione et al., Br. J. Pharmacal., 2011, vol. 162, pp. 584-596 (Year: 2011).

Becker et al., "Acute Effects of Psilocybin After Escitalopram or Placebo Pretreatment in a Randomized, Double-Blind, Placebo-Controlled, Crossover Study in Healthy Subjects," Clinical Pharmacology & Therapeutics, vol. 0, No. 0, Nov. 2, 2021.

Zhuk et al., "Research on Acute Toxicity and the Behavioral Effects of Methanolic Extract from Psilocybin Mushrooms and Psilocin in Mice", Toxins, 2015, pp. 1018-1029, 7(4).

Sard et al. "SAR of psilocybin analogs: discovery of a selective 5-HT 2C agonist", . Bioorg Med Chem Lett., 2005, pp. 4555-4559, 15(20).

Ross et al., "Rapid and sustained symptom reduction following psilocybin treatment for anxiety and depression in patients with life-threatening cancer: a randomized controlled trial", Journal of Psychopharmacology, 2016, pp. 1165-1180, 30(12).

Rambousek et al., "The effect of psilocin on memory acquisition, retrieval, and consolidation in the rat", Front. Behav. Neurosci., 2014, 8(180).

Tyls et al., "Psilocybin—summary of knowledge and new perspectives", Eur Neuropsychopharmacol, 2014, pp. 342-356, 24(3).

Stebelska, "Fungal Hallucinogens Psilocin, Ibotenic Acid, and Muscimol: Analytical Methods and Biologic Activities", Ther Drug Monit., 2013, pp. 420-442, 35(4).

Matsushima et al., "Historical overview of psychoactive mushrooms", Inflammation and Regeneration, 2009, pp. 47-58, 29(1).

"Amount of Niacin in Mushrooms" (http://www.dietandfitnesstoday.com/niacin-in-mushrooms.php; 12 pages) (Accessed Feb. 1, 2022)(Year: 2022).

Bigwood, J_ et al., "Variation of Psilocybin and Psilocin Levels with Repeated Flushes (Harvests) of MatureSporocarps of Psilocybe Cubensis (Earle) Singer," Journal of Ethnopharmacology, vol. 5 No. 3, pp. 287-291 (1982).

Chadeayne et al., "Norpsilocin: freebase and fumarate salt," Acta Crystallogr. E Crystallogr. Commun., Mar. 27, 2020;76(Pt 4) :589-593 (Year: 2020).

Daniel, J., et al., 'Clinical potential of psilocybin as a treatment for mental health conditions', Mental Health Clinician, 2017, vol. 1, p. 24-28.

Dutton, Gail, Field Trip Health's New Psilocybin Research Facility Probes the Secrets of Shrooms, BioSpace, Pub. Feb. 26, 2021, https://www.biospace.com/article/field-trip-health-s-new-psilocybin-research-facility-probes-the-secrets-of-shrooms/.

Griffiths et al. "Psilocybin produces substantial and sustained decreases in depression and anxiety in patients with life-threatening cancer: A randomized double-blink trial." Journal of Psychopharmacology, 30 (12), 2016; pp. 1181-1197.

Hanes, K. R., 'Serotonin, Psilocybin, and Body Dysmorphic Disorder: A Case Report', Journal of Clinical Psychopharmacology, 1996, vol. 16(2), p. 188-189.

International Preliminary Report on Patentability in International Application No. PCT/US2018/061385, dated May 19, 2020.

International Search Report in International Application No. PCT/US2018/061385, dated Feb. 1, 2019.

Kasper et al. "Silexan in anxiety disorders: Clinical data and pharmacological background," The World Journal of Biological Psychiatry, 2018, 19:6, pp. 412-420 (Published Online Jun. 19, 2017) (Year:2018).

Lenz et al. "Identification of w-N-Methyl-4-hydroxytryptamine (Norpsilocin) as a Psilocybe Natural Product", J. Nat. Prod., 2017, vol. 80, pp. 2835-2838 (Year: 2017).

Li, I-Chen et al., "Neurohealth Properties of Hericium erinaceus Mycelia Enriched with Erinacines," Behavioural Neurology, vol. 2018, pp. 1-11 (2018).

Ma et al. "Hericenones and erinacines: stimulators of nerve growth factor (NGF) biosynthesis in Hericium erinaceus," Mycology, vol. 1, No. 2, 2010; pp. 92-98.

Mahmood "Bioactive Alkaloids from Fungi: Psilocybin", Chapter 18 in book Natural Products, K.G. Ramawat, J.M. Merillon (eds.),2013, pp. 523-552 (Year: 2013).

Nichols et al. "Psychedelics as Medicines: An Emerging New Paradigm", Clinical Pharmacology & Therapeutics, Feb. 2017, vol. 101, No. 2, pp. 209-219 (Year: 2017).

PsyBio Therapeutics Corp., PsyBio Therapeutics Initiates Process Development of Proprietary Biosynthetic Norbaeocystin, Mar. 23, 2021, https://www.newswire.ca/news-releases/psybio-therapeutics-initiates-process-development-of-proprietary-biosynthetic-norbaeocystin-804305281.html.

Quednow, B. B, et al., 'Psilocybin-Induced Deficits in Automatic and Controlled Inhibition are Attenuated by Ketanserin in Healthy Human Volunteers', Neuropsychopharmacology, 2012, vol. 37, p. 630-640.

Russo, "Taming THC: potential cannabis synergy and phytocannabinoid-terpenoid entourage effects," (British Journal of Pharmacology, 2011, vol. 163, pp. 1344-1364) (Year: 2011).

Sanchez "Bioactives from Mushroom and Their Application" (2017) in book Food Bioactives, M. Puri (ed), pp. 23-57 (Year:2017).

(56) References Cited

OTHER PUBLICATIONS

Schuwald et al., "Lavender Oil-Potent Anxiolytic Properties via Modulating Voltage Dependent Calcium Channels," PLoS ONE, 2013, vol. 8, No. 4, e59998, doi: 10.1371/journal.pone.0059998, 9 pages (Year: 2013).
Sherwood et al. "Synthesis and Biological Evaluation of Tryptamines Found in Hallucinogenic Mushrooms: Norbaeocystin, Baeocystin, Norpsilocin, and Aeruginascin", J. Nat. Prod., 2020, vol. 83, pp. 461-467 (Year: 2020).
Thomas et al., "Combination Therapy with Monoamine Oxidase Inhibitors and Other Antidepressants or Stimulants: Strategies for the Management of Treatment-Resistant Depression," Pharmacotherapy, 2015, vol. 35, No. 4, pp. 433-449 (Year: 2015).
Wink, "Modes of Action of Herbal Medicines and Plant Secondary Metabolites," (Medicines, 2015, vol. 2, pp. 251-286) (Year: 2015).
Bauer, "Scientists Synthesize and Test the Magic Mushroom Compounds Baeocystin, Norbaeocystin, Norpsilocin, and Aeruginascin," Psychedelic Science Review, Mar. 5, 2020, https://psychedelicreview.com/scientists-synthesize-and-test-the-magic-mushroom-compounds-baeocystin-norbaeocystin-norpsilocin-and-aeruginascin/.
Licht et al, Simultaneous polysubstance use among Danish 3,4-methylenedioxymethamphetamine and hallucinogen users: combination patterns and proposed biological bases, vol. 27 pp. 352-363, May 3, 2012, Human Psychopharmacology Clinical and Experimental.
White, Mixing DXM and Other Drugs, 2015; retrieved from Web Archive, Erowid, Mixing DXM and other Drugs page, Apr. 22, 2015, https://web.archive.org/web/20150422070624/https://www.erowid.org/chemicals/dxm/faq/dxm_mixing.shtml.
Fozard et al, Dual mechanism of the stimulant action of N,N-dimethyl-5-hydroxytryptamine (bufotenine) on cardiac sympathetic nerves, vol. 49(1) pp. 25-30, Jan. 20, 1978, European Journal of Pharmacology.
Tittarelli et al, Recreational Use, Analysis and Toxicity of Tryptamines, vol. 13 pp. 26-46, 2015, Current Neuropharmacology.
Schechter, 'Candyflipping': Synergistic discriminative effect of LSD and MDMA, vol. 314 pp. 131-134, 1998, European Journal of Pharmacology.
Ott, Human Pharmacology of Oral DMT Plus Harmine, vol. 31 (2) pp. 171-177, 1999 Journal of Psychoactive Drugs.
Boys et al, Understanding reasons for drug use amongst young people a functional perspective, vol. 16(4) pp. 457-459, 2001, Health Education Research.
Shulgin et al, Tihkal: Tryptamines I Have Known and Loved: The Chemistry Continues, Chapter 48 line 256-261, 1997, Transform Press.
Chilton et al, Psilocin, Bufotenine and Serotonin: Historical and Biosynthetic Observations, vol. 11 (1-2) pp. 61-69, Jan. 1979, Journal of Psychedelic Drugs.
Barrett et al, Patterns of simultaneous polysubstance use in drug using university students, vol. 21 pp. 255-263, Apr. 6 2006, Human Psychopharmacology Clinical and Experimental.
Ebersole et al., "Molecular Basis of Partial Agonism: Orientation of Indoleamine Ligands in the Binding Pocket of the Human Serotonin 5-HT2A Receptor Determines Relative Efficacy," Molecular Pharmacology, 2003, vol. 63, pp. 36-43 (Year: 2003).
Kawagishi et al., "Erinacines A, B and C, strong stimulators of nerve growth factor (NGF)-synthesis, from the mycelia of Hericium erinaceum," Tetrahedron Letters, 1994, vol. 35, No. 10, pp. 1569-1572 (Year: 1994).
Gukasyan et al., "Attenuation of Psilocybin Mushroom Effects During and After SSRI-SNRI Antidepressant Use", Journal of Psychopharmacology, 00(0), 1-10, 2023.
Lane, et al., "Selective Serotonin Reuptake Inhibitor-Induced Serotonin Syndrome: Review", Journal of Clinical Psychopharmacology, 17(3), 208-221, 1997.
Rafael G. dos Santos et al. "Antidepressive, anxiolytic, and antiaddictive effects of ayahuasca, psilocybin and lysergic acid diethylamide (LSD): a systematic review of clinical trials published in the last 25 years." Ther Adv. Psychopharmacol, 2016, vol. 6[3], p. 193-213.

* cited by examiner

COMPOSITIONS AND METHODS COMPRISING A COMBINATION OF SEROTONERGIC DRUGS

CROSS REFERENCE TO OTHER RELATED APPLICATIONS

This application is a continuation in part of U.S. application Ser. No. 15/893,562, filed Feb. 9, 2018, which claims benefit under 35 U.S.C. 119(e) to U.S. Provisional Application No. 62/457,123, filed Feb. 9, 2017, U.S. Provisional Application No. 62/587,395, filed Nov. 16, 2017, U.S. Provisional Application No. 62/587,410, filed Nov. 16, 2017, U.S. Provisional Application No. 62/587,419, filed Nov. 16, 2017, U.S. Provisional Application No. 62/587,431, filed Nov. 16, 2017, U.S. Provisional Application No. 62/592,307, filed Nov. 29, 2017, U.S. Provisional Application No. 62/592,320, filed Nov. 29, 2017, U.S. Provisional Application No. 62/593,021, filed Nov. 30, 2017, U.S. Provisional Application No. 62/595,321, filed Dec. 6, 2017, U.S. Provisional Application No. 62/595,336, filed Dec. 6, 2017, U.S. Provisional Application No. 62/598,767, filed Dec. 14, 2017, U.S. Provisional Application No. 62/609,115, filed Dec. 21, 2017, and U.S. Provisional Application No. 62/613,360, filed Jan. 3, 2018, which are all hereby incorporated by reference in their entirety.

TECHNICAL FIELD

This disclosure relates to serotonergic drugs, combinations thereof, and methods of using them for treating and preventing a variety of human conditions.

BACKGROUND

Many people worldwide are afflicted with psychological or mood disorders, such as depression, anxiety, compulsion, and post-traumatic stress disorders. Many of these conditions are believed to involve a person's serotonin system—including interactions between (A) the neurotransmitter serotonin (often abbreviated 5-HT) and (B) several different subtypes of serotonin neurotransmitter receptors found in the human body.

A variety of compositions are known to modulate activity at the serotonin receptors. A number of pharmaceuticals (antidepressants, serotonin reuptake inhibitors, selective serotonin reuptake inhibitors, etc.) have become available. In 2014, the Better Communication Company projected the global market for drugs treating mental disorders to be about $77.1 billion by 2018, and register a five-year compound annual growth rate of 2.3% from 2013 to 2018. Almost all these pharmaceuticals target neurotransmitters, e.g., serotonergic receptors, adrenergic receptors, dopaminergic receptors, etc., and in different ways. All ten of the leading pharmaceutical products for treating mood disorders (such as depression, obsessive compulsive disorder, and/or anxiety disorders) target serotonin pathways.

However, despite their unquestionable popularity and commercial success, the users of these pharmaceutical products are unsatisfied with their long onset times, severe side-effects, and poor efficacy. In many cases, these drugs are harmful to the user. For example, many people taking prescription drugs targeting serotonin report feeling suicidal thoughts, sexual dysfunction, fatigue, elevated blood pressure, blurred vision, abnormal heart rate, nausea, and weight gain.

So-called "magic mushrooms" are taken recreationally by millions of people in the United States. Psilocybin (also known as 4-phosphoryloxy-N,N-dimethyltryptamine or [3-(2-trimethylaminoethyl)-1H-indol-4-yl] dihydrogen phosphate) is considered to be the most abundant psychoactive compound within a "magic mushroom." Psilocin (4-hydroxy-N, N-dimethyltryptamine) is considered to be the second most abundant compound. Many within the scientific community consider psilocin to be the only active ingredient in "magic mushrooms," reasoning that psilocybin serves only as a prodrug and does not have activity itself. No conclusive studies have been conducted to support or undermine this theory.

Formulated and administered correctly, psilocin and psilocybin provide fast-acting and long-lasting changes to a person's mood. These effects can be accomplished with only minor side effects, low potential for addiction, low potential for abuse, and low risk of toxicity.

Currently the state of the art for psilocybin technology is not advanced. Despite a handful of studies utilizing purified psilocybin as a single active pharmaceutical ingredient, virtually no work has been done formulating psilocybin into drug products for treating mental disorders. Aside from a few studies on purified psilocybin, no efforts have been made to modulate its properties with formulating agents or other ingredients. No efforts have been made to formulate particular combinations or doses of psilocybin derivatives or combinations with other active molecules. No efforts have been made to formulate psilocybin into compositions capable of modifying activity at one or more neurotransmitter receptors.

The psilocybin arts focus primarily on cultivating and consuming mushrooms. Unfortunately, collecting and ingesting mushrooms can be dangerous because of difficulties distinguishing the desired mushroom species from similar looking species. For example, mushrooms of the genus *psilocybe* are easily confused with toxic lookalikes. Mistaken identification of *psilocybe* mushrooms leads to cases of serious illness and death every year.

Even when "magic mushrooms" are properly identified, those mushrooms vary greatly in terms of the concentration of psilocybin, psilocin, and other (often overlooked) active ingredients. Accordingly, administering a specific compound or a particular dose using mushrooms is not possible because of the variability in the chemical composition of mushrooms.

Additionally, even when "magic mushrooms" are properly identified, they are prone to contamination. Contamination can result in problems, such as unwanted side effects like "wood lover paralysis."

Very little work has been done with psilocybin pharmacology because of the art's general understanding not to pursue psilocybin formulations. To the contrary, the current state of the art focuses almost exclusively on "magic mushrooms." The highest authorities on the subject in the United States still maintain that psilocybin has "no beneficial purpose" and carries a "high potential for abuse."

Until recently, very little work had been done in developing therapeutic methods comprising psilocybin. Recent efforts have shown that taking pure isolated psilocybin shows promise for treating several psychological conditions, such as post-traumatic stress, anxiety, addiction, depression, and compulsion.

On Nov. 6, 2017 Newsweek Magazine explained the state of the art as follows: "Magic mushrooms ('active psilocybin') were used as experimental medical treatment in the 1960s, and some researchers are again looking to them for healing. For example, in a pilot study in 2011, mushrooms appeared to have a positive effect on cancer patients with anxiety. In 2016, a study demonstrated their use in treating depression."

Because psilocybin research is a relatively small area, virtually no work has been done formulating psilocybin or studying the pharmacology of psilocybin, its derivatives, and new formulations comprising them. Properly studying, formulating, and dosing psilocybin and its derivatives would provide significant benefits in treating mood and neurological disorders, such as depression, attention deficit hyperactivity disorder, compulsive disorder, and/or an anxiety disorder.

There exists a need for new compositions and methods comprising one or more of 3-(2-Dimethylaminoethyl)-1H-indol-4-yl] dihydrogen phosphate, 4-hydroxy-N,N-dimethyltryptamine, [3-(2-trimethylaminoethyl)-1H-indol-4-yl] dihydrogen phosphate, 4-hydroxy-N,N,N-trimethyltryptamine, [3-(2-methylaminoethyl)-1H-indol-4-yl] dihydrogen phosphate, 4-hydroxy-N-methyltryptamine, [3-(aminoethyl)-1H-indol-4-yl] dihydrogen phosphate, and/or 4-hydroxytryptamine in a precise dosage formulation.

There further exists a need for formulations combining these formulations with other molecules affecting the activity of neurotransmitters, e.g., serotonergic drugs like LSD and/or MDMA.

There exists a need for better methods and compositions for targeting and/or modulating activity at one or more neurotransmitter receptors. Recently, "magic mushrooms" and one molecule contained within them have shown potential application in this area. However, before these molecules can be made into effective treatments, they need to be properly studied and formulated into compositions that provide consistent and specific effects, e.g., particular activity at a neurotransmitter receptor.

Accordingly, the state of the art for psilocybin art has an unmet need for formulated psilocybin compositions. This need can be met by isolating and identifying the molecules in magic mushrooms and studying their activity using cellular pharmacology.

Lysergic acid diethylamide ("LSD") is a synthetic serotonergic psychedelic. Like psilocybin derivatives, the psychedelic effects of LSD are mainly attributed to its potent partial serotonin (5-HT) 5-HT2A receptor agonism. The effects of LSD have been frequently investigated in the past in both healthy participants and patients. Several of these studies described robust and sustained effects of LSD in patients suffering from addiction, anxiety, and depression. The acute subjective effects elicited by LSD are mostly positive in humans. The compound 3,4-methylenedioxymethamphetamine (MDMA) is a serotonergic drug that enhances serotonergic neurotransmission via release of 5-HT through the serotonin transporter (SERT). MDMA is also known to trigger oxytocin release which may contribute to its effects to increase trust, prosociality, and enhanced empathy.

Although psychedelics (e.g., psilocybin derivatives, LSD, DMT, and other tryptamines) have significant potential for treating many mood disorders, such treatment options often have side-effects which can be generally categorized as "dysphoria." This dysphoric or unpleasant subjective effects include negative thoughts, rumination, anxiety, panic, paranoia, loss of trust towards other people and perceived loss of control, depending on the dose of the psychedelic drug used, the personality traits of the person consuming it (i.e. 'set'), the environment in which it is consumed (i.e. 'setting'), and other factors yet to be determined.

Acute negative psychological effects are considered the main risk of psychedelic substance use in humans. There is an unmet need for mitigating these acute negative psychological effects when administering psychedelic drugs to human subjects. There is an unmet need for methods which are capable of reducing bad drug effects while enhancing good drug effects to optimize a psychedelic experience.

DETAILED DESCRIPTION

Disclosed herein are new compositions and methods which comprise a therapeutically effective amount of a first serotonergic drug and a therapeutically effective amount of a second serotonergic drug. In one embodiment, the disclosed compositions and methods comprise a psilocybin derivative. In one embodiment, the compositions and methods disclosed herein comprise one or more psilocybin derivatives chosen from the following: [3-(2-Dimethylaminoethyl)-1H-indol-4-yl] dihydrogen phosphate, 4-hydroxytryptamine, 4-hydroxy-N,N-dimethyltryptamine, [3-(2-methylaminoethyl)-1H-indol-4-yl] dihydrogen phosphate, 4-hydroxy-N-methyltryptamine, [3-(aminoethyl)-1H-indol-4-yl] dihydrogen phosphate, [3-(2-trimethylaminoethyl)-1H-indol-4-yl] dihydrogen phosphate, and 4-hydroxy-N,N,N-trimethyltryptamine.

In one embodiment, the compositions and methods disclosed herein comprise one or more purified psilocybin derivatives chosen from: [3-(2-Dimethylaminoethyl)-1H-indol-4-yl] dihydrogen phosphate, 4-hydroxytryptamine, 4-hydroxy-N,N-dimethyltryptamine, [3-(2-methylaminoethyl)-1H-indol-4-yl] dihydrogen phosphate, 4-hydroxy-N-methyltryptamine, [3-(aminoethyl)-1H-indol-4-yl] dihydrogen phosphate, [3-(2-trimethylaminoethyl)-1H-indol-4-yl] dihydrogen phosphate, and 4-hydroxy-N, N, N-trimethyltryptamine.

In one embodiment, the compositions and methods disclosed herein comprise LSD. In one embodiment, the compositions and methods disclosed herein comprise MDMA.

In one embodiment, the methods and compositions disclosed herein comprise regulating the activity of a neurotransmitter receptor with a first dosage formulation comprising a first purified psilocybin derivative. In one embodiment, the methods and compositions disclosed herein comprise administering a first dosage formulation comprising a second purified psilocybin derivative. In one embodiment, the methods disclosed herein comprise administering a first dosage formulation comprising a first purified cannabinoid. In one embodiment, the methods disclosed herein comprise administering a first dosage formulation comprising a first purified terpene. In one embodiment, the methods disclosed herein comprise administering a first dosage formulation comprising a neurotransmitter activity modulator. In one embodiment, the methods disclosed herein comprise administering a first dosage formulation comprising a first purified psilocybin derivative, a first purified cannabinoid, a first purified terpene, and/or a neurotransmitter activity modulator.

In one embodiment, the methods disclosed herein comprise administering the compositions disclosed herein. In one embodiment, the methods disclosed herein comprise treating a psychological disorder, e.g., an anxiety disorder, a compulsive disorder, a depressive disorder, etc., with the compositions disclosed herein, e.g., a composition with one or more psilocybin derivatives, a composition with one or more cannabinoids, a composition with one or more terpenes, and/or a combination thereof. In one embodiment, the methods disclosed herein comprise treating a psychological disorder, e.g., an anxiety disorder, a compulsive disorder, a depressive disorder, etc., with the compounds and compositions disclosed herein and a neurotransmitter activity modulator, e.g., a serotonergic drug, a dopaminergic drug, etc.

Disclosed herein are new compositions and methods comprising a therapeutically effective amount of a first serotonergic drug and a therapeutically effective amount of a second serotonergic drugs, In one embodiment, the compositions and methods comprise a first serotonergic drug, which is purified psilocybin derivative and serotonergic drug which is not the same as the first purified psilocybin derivative. In one embodiment, the compositions disclosed herein comprise a first purified psilocybin derivative and a serotonergic drug present in purposefully engineered and unnaturally occurring molar ratios. In one embodiment, the first serotonergic drug is chosen from 6-Allyl-N,N-diethyl-NL, N,N-Dibutyl-T, N,N-Diethyl-T, N,N-Diisopropyl-T, 5-Methyoxy-alpha-methyl-T, N,N-Dimethyl-T, 2,alpha-Dimethyl-T, alpha,N-Dimethyl-T, N,N-Dipropyl-T, N-Ethyl-N-isopropyl-T, alpha-Ethyl-T, 6,N,N-Triethyl-NL, 3,4-Dihydro-7-methoxy-1-methyl-C, 7-Methyoxy-1-methyl-C, N,N-Dibutyl-4-hydroxy-T, N,N-Diethyl-4-hydroxy-T, N,N-Diisopropyl-4-hydroxy-T, N,N-Dimethyl-4-hydroxy-T, N,N-Dimethyl-5-hydroxy-T, N,N-Dipropyl-4-hydroxy-T, N-Ethyl-4-hydroxy-N-methyl-T, 4-Hydroxy-N-isopropyl-N-methyl-T, 4-Hydroxy-N-methyl-N-propyl-T, 4-Hydroxy-N,N-tetramethylene-T Ibogaine, N,N-Diethyl-L, N-Butyl-N-methyl-T, N,N-Diisopropyl-4,5-methylenedioxy-T, N,N-Diisopropyl-5,6-methylenedioxy-T, N,N-Dimethyl-4,5-methylenedioxy-T, N,N-Dimethyl-5,6-methylenedioxy-T, N-Isopropyl-N-methyl-5,6-methylenedioxy-T, N,N-Diethyl-2-methyl-T, 2,N,N-Trimethyl-T, N-Acetyl-5-methoxy-T, N,N-Diethyl-5-methoxy-T, N,N-Diisopropyl-5-methoxy-T, 5-Methoxy-N,N-dimethyl-T, N-Isopropyl-4-methoxy-N-methyl-T, N-Isopropyl-5-methoxy-N-methyl-T, 5,6-Dimethoxy-N-isopropyl-N-methyl-T, 5-Methoxy-N-methyl-T, 5-Methoxy-N,N-tetramethylene-T, 6-Methoxy-1-methyl-1,2,3,4-tetrahydro-C, 5-Methoxy-2,N,N-trimethyl-T, N,N-Dimethyl-5-methylthio-T, N-Isopropyl-N-methyl-T, alpha-Methyl-T, N-Ethyl-T, N-Methyl-T, 6-Propyl-NL, N,N-Tetramethylene-T, Tryptamine, and 7-Methoxy-1-methyl-1,2,3,4-tetrahydro-C, and alpha,N-Dimethyl-5-methoxy-T.

In one embodiment the first serotonergic drug is chosen from alprazolam, amphetamine, aripiprazole, azapirone, a barbiturate, bromazepam, bupropion, buspirone, a cannabinoid, chlordiazepoxide, citalopram, clonazepam, clorazepate, dextromethorphan, diazepam, duloxetine, escitalopram, fluoxetine, flurazepam, fluvoxamine, lorazepam, lysergic acid diethylamide, lysergamide, 3,4-methylenedioxymethamphetamine, milnacipran, mirtazapine, naratriptan, paroxetine, pethidine, phenethylamine, psicaine, oxazepam, reboxetine, serenic, serotonin, sertraline, temazepam, tramadol, triazolam, a tryptamine, venlafaxine, and vortioxetine. In one embodiment of the compositions and methods disclosed herein, the first serotonergic drug is a psilocybin derivative. In one embodiment of the compositions and methods disclosed herein, the first serotonergic drug is a psilocybin derivative and the second serotonergic drug is MDMA. In one embodiment, the first serotonergic drug is LSD and the second serotonergic drug is MDMA. In one embodiment, the compositions disclosed herein comprise a combination of LSD and MDMA within a single dosage formulation. In one embodiment, the methods disclosed herein comprise administering LSD and MDMA in a single dosage formulation. In one embodiment, the methods disclosed herein comprise administering LSD and MDMA in separate dosage formulations.

Disclosed herein are new compositions and methods comprising a first purified psilocybin derivative and a first purified cannabinoid. In one embodiment, the compositions disclosed herein comprise a first purified psilocybin derivative and a first purified cannabinoid present in purposefully engineered and unnaturally occurring molar ratios.

Disclosed herein are new compositions comprising a first purified psilocybin derivative and a first purified terpene. In one embodiment, the compositions disclosed herein comprise a first purified psilocybin derivative and a first purified terpene present in purposefully engineered and unnaturally occurring molar ratios.

Disclosed herein are new compositions comprising a first purified psilocybin derivative, a first purified cannabinoid, and a first purified terpene. In one embodiment, the compositions disclosed herein comprise a first purified psilocybin derivative, a first purified cannabinoid, and a first purified terpene present in purposefully engineered and unnaturally occurring molar ratios.

Disclosed herein are new compositions comprising a first purified psilocybin derivative, a first purified cannabinoid, and a second purified cannabinoid. In one embodiment, the compositions disclosed herein comprise a first purified psilocybin derivative, a first purified cannabinoid, and a second purified cannabinoid present in purposefully engineered and unnaturally occurring molar ratios.

As used herein, the term "chitin" refers to a polymer found primarily in the cell walls of fungi. In one embodiment, chitin is translucent. In one embodiment, chitin is pliable. In one embodiment, chitin is resilient. In one embodiment, chitin is durable. In one embodiment, chitin comprises nitrogen. In one embodiment, the compositions disclosed herein comprise between 0-10 mass percent of chitin as determined by dry weight. In one embodiment, the compositions disclosed herein comprise between 0-5 mass percent of chitin as determined by dry weight. In one embodiment, the compositions disclosed herein comprise less than 1 mass percent of chitin as determined by dry weight.

In one embodiment, the compositions disclosed herein comprise between 0-15 mass percent of water as determined by dry weight. In one embodiment, the compositions disclosed herein comprise between 0-10 mass percent of water as determined by dry weight. In one embodiment, the compositions disclosed herein comprise between 0-5 mass percent of water as determined by dry weight. In one embodiment, the compositions disclosed herein comprise between 0-1 mass percent of water as determined by dry weight.

As used herein, the term "protein" refers to a large molecule comprising one or more amino acid chains (polypeptides). In one embodiment, a protein performs a function within an organism, e.g., catalysing metabolic reactions, facilitating DNA replication, responding to stimuli, transporting molecules, etc. In one embodiment, a protein serves as a structural component in an organism.

In one embodiment, the compositions disclosed herein comprise between 0-15 mass percent of protein as determined by dry weight. In one embodiment, the compositions disclosed herein comprise between 0-10 mass percent of protein as determined by dry weight. In one embodiment, the compositions disclosed herein comprise between 0-5 mass percent of protein as determined by dry weight. In one embodiment, the compositions disclosed herein comprise between 0-1 mass percent of protein as determined by dry weight. In one embodiment, the compositions disclosed herein comprise less than 5 mass percent of protein as determined by dry weight.

As used herein, the term "dry weight" refers to a measurement of the mass of a sample after removing all, or substantially all, the liquid from the sample. In one embodiment, removing liquid comprises dehydrating, heating, stirring, filtering, and/or any other method suitable for liquid water. In one embodiment, dry weight is measured by pounds. In one embodiment, dry weight is measured by ounces. In one embodiment, dry weight is measured by grams, e.g., milligrams, kilograms, etc.

In one embodiment, the compositions disclosed herein are in the form of a dried powder.

As used herein, the term "dried powder" refers to a substance composed of fine particles and comprising little or no liquid material. In one embodiment, a dried powder is derived by evaporating alcohol from a solution leaving behind dried particles. In one embodiment, a dried powder is a precipitate from a solution. In one embodiment, a dried powder is a solid collected from a plant (e.g., mushrooms) and pulverized into a powder, e.g., using a mortar and pestle.

In one embodiment, a dried powder is composed of particles with a crystalline structure.

In one embodiment, a dried powder is composed of pure crystals.

In one embodiment, a dried powder is composed of a mixture of crystals.

Within the context of this disclosure, any method for removing liquid is suitable for making a dried powder, e.g., heating, mixing, filtering, evaporating, etc.

In one embodiment, the compounds disclosed herein are in a dried powder form, e.g., a psilocybin derivative, a cannabinoid, a terpene, etc.

In one embodiment, a dried powder comprises an anti-clumping agent, e.g., a desiccant.

Within the context of this disclosure, it is understood that a sample may comprise small amounts of liquid that are negligible in the final measurement of a sample. In one example, it is acceptable for a composition of this disclosure to comprise as much as 1% water as measured by mass percent.

As used herein, the term "mass percent", aka "percent by mass", "mass %", etc., refers to the amount of a compound relative to the entire mass of a sample as a fraction of 100. In one embodiment, mass percent is calculated with the following formula for a compound of interest:

(mass of compound of interest in grams)/(total mass of composition in grams)×100%

In one example, a composition weighs 100 g and comprises 0.5 g of a first purified psilocybin derivative, 8 g of a first purified cannabinoid, and 2.5 g of a first purified terpene. The mass percent of the first purified psilocybin derivative, the first purified cannabinoid, and the first purified terpene are 0.5%, 8%, and 2.5% respectively.

In one example, for a 25 g composition comprising 2 g of a psilocybin derivative. The amount of a psilocybin derivative within a composition is determined by the following:

2.0 g of psilocybin derivative÷25.0 g of composition×100%=8.0%

Within the context of this disclosure, the term "purified" means separated from other materials, such as plant or fungal material, e.g., protein, chitin, cellulose, or water. In one embodiment, the term "purified" refers to a compound substantially free of other materials. In one embodiment, the term "purified" refers to compound that is substantially free from a second tryptamine compound. In one embodiment, the term "purified" refers to a compound substantially free from histidine. In one embodiment, the term "purified" refers to a compound substantially free from a biological material, such as mold, fungus, plant mater, or bacteria. In one embodiment, the term "purified" refers to a compound substantially free from a paralytic.

In one embodiment, the term "purified" refers to a compound or composition that has been crystallized.

In one embodiment, the term "purified" refers to a compound or composition that has been chromatographed, for example by gas chromatography, liquid chromatography (e.g., LC, HPLC, etc.), etc.

In one embodiment, the term "purified" refers to a compound or composition that has been distilled.

In one embodiment, the term "purified" refers to a compound or composition that has been sublimed.

In one embodiment, the term "purified" refers to a compound or composition that has been subject to two or more steps chosen from: crystallization, chromatography, distillation, or sublimation.

In one embodiment, the term "purified" refers to a compound that is between 80-100% pure, meaning that the compound makes up 80-100% of the total mass of the composition.

In one embodiment, the term "purified" refers to a compound that is between 90-100% pure, meaning that the compound makes up 90-100% of the total mass of the composition.

In one embodiment, the term "purified" refers to a compound that is between 95-100% pure, meaning that the compound makes up 95-100% of the total mass of the composition.

In one embodiment, the term "purified" refers to a compound that is between 99-100% pure, meaning that the compound makes up 99-100% of the total mass of the composition.

In one embodiment, the term "purified" refers to a compound that is between 99.9-100% pure, meaning that the compound makes up 99.9-100% of the total mass of the composition.

Additionally, the compounds disclosed herein are often found in so-called "conjugated" or "derivatized" forms during chemical analysis. In one example, a psilocybin derivative is in the form of a glucuronide derivative in human serum assays. Enzymatic hydrolysis converts the glucuronide derivative into a non-glucuronide form. Prior to extraction, hydrolysis of the glucuronide derivative can be useful.

For example, one can deduce the concentration of psilocin by GC/MS by using beta-glucuronidase for liberating psilocin from its conjugated (aka glucuronide derivative form) in urine and then using MSTFA (N-methyl-N-trimethylsilyltrifluoroacetamide) for derivatization of psilocin to its trimethylsilyl derivative.

GC/MS can be used for identification and quantification of psilocin in biological specimens.

Psilocin and psilocybin can also be identified by using liquid chromatography with or without tandem mass spectrometry (LC/MS/MS). When using LC/MS, method derivatization prior to analysis is often not required. Liquid chromatography combined with tandem mass spectrometry for analysis of psilocin and psilocybin in psychoactive mushrooms may also provide useful samples. All data indicates that the presence and amount of psychoactive compounds within naturally occurring samples is considered to be highly variable.

Disclosed herein are new compositions comprising particular ratios of [3-(2-Dimethylaminoethyl)-1H-indol-4-yl] dihydrogen phosphate, 4-hydroxy-N,N-dimethyltryptamine, [3-(2-trimethylaminoethyl)-1H-indol-4-yl] dihydrogen phosphate, 4-hydroxy-N,N,N-trimethyltryptamine, [3-(2-methylaminoethyl)-1H-indol-4-yl] dihydrogen phosphate, 4-hydroxy-N-methyltryptamine, [3-(aminoethyl)-1H-indol-4-yl] dihydrogen phosphate, and/or 4-hydroxytryptamine; and their salts and derivatives.

As used herein, the term "particular ratio" refers to the amount of a compound in relation to the amount of another compound or compounds. In one embodiment, there is a about 1:1 ratio of [3-(2-Dimethylaminoethyl)-1H-indol-4-yl] dihydrogen phosphate to 4-hydroxy-N,N-dimethyltryptamine. In one embodiment, a particular ratio of compounds is measured by the same unit, e.g., grams, kilograms, pounds, ounces, etc. In one embodiment, a particular ratio of compounds is measured in moles, i.e., molar proportions or molar ratios.

In one example, there is a particular ratio of 1 kilogram to 2 grams of [3-(2-Dimethylaminoethyl)-1H-indol-4-yl] dihydrogen phosphate to 4-hydroxy-N,N-dimethyltryptamine.

Disclosed herein are new compositions comprising particular amounts of [3-(2-Dimethylaminoethyl)-1H-indol-4-yl] dihydrogen phosphate, 4-hydroxy-N,N-dimethyltryptamine, [3-(2-trimethylaminoethyl)-1H-indol-4-yl] dihydrogen phosphate, 4-hydroxy-N,N,N-trimethyltryptamine, [3-(2-methylaminoethyl)-1H-indol-4-yl] dihydrogen phosphate, 4-hydroxy-N-methyltryptamine, [3-(aminoethyl)-1H-indol-4-yl] dihydrogen phosphate, and/or 4-hydroxytryptamine; and their salts and derivatives.

As used herein, the term "particular amount" refers to the quantity of a compound or compounds. In one embodiment, a particular amount is the combined quantity of two compounds within a sample. In one embodiment, a particular amount is measured by dry weight. In one embodiment, the particular amount has 1, 2, 3, or 4 significant figures.

Disclosed herein are new compositions comprising little or no deviation (between samples of the said compositions) of one or more of the following molecules: [3-(2-Dimethylaminoethyl)-1H-indol-4-yl] dihydrogen phosphate, 4-hydroxy-N,N-dimethyltryptamine, [3-(2-trimethylaminoethyl)-1H-indol-4-yl] dihydrogen phosphate, 4-hydroxy-N,N,N-trimethyltryptamine, [3-(2-methylaminoethyl)-1H-indol-4-yl] dihydrogen phosphate, 4-hydroxy-N-methyltryptamine, [3-(aminoethyl)-1H-indol-4-yl] dihydrogen phosphate, and/or 4-hydroxytryptamine; and their salts and derivatives.

Disclosed herein is a new composition, comprising:
a first purified psilocybin derivative; wherein the first purified psilocybin derivative is chosen from [3-(2-Dimethylaminoethyl)-1H-indol-4-yl] dihydrogen phosphate, 4-hydroxy-N,N-dimethyltryptamine, [3-(2-methylaminoethyl)-1H-indol-4-yl] dihydrogen phosphate, 4-hydroxy-N-methyltryptamine, [3-(aminoethyl)-1H-indol-4-yl] dihydrogen phosphate, 4-hydroxytryptamine, [3-(2-trimethylaminoethyl)-1H-indol-4-yl] dihydrogen phosphate, and 4-hydroxy-N,N,N-trimethyltryptamine; and
a second purified psilocybin derivative; wherein the second purified psilocybin derivative is chosen from [3-(2-Dimethylaminoethyl)-1H-indol-4-yl] dihydrogen phosphate, 4-hydroxy-N,N-dimethyltryptamine, [3-(2-methylaminoethyl)-1H-indol-4-yl] dihydrogen phosphate, 4-hydroxy-N-methyltryptamine, [3-(aminoethyl)-1H-indol-4-yl] dihydrogen phosphate, 4-hydroxytryptamine, [3-(2-trimethylaminoethyl)-1H-indol-4-yl] dihydrogen phosphate, and 4-hydroxy-N,N,N-trimethyltryptamine.

In one embodiment, the compositions disclosed herein comprise a molar ratio between about 10:1 to about 1:10 of the first purified psilocybin derivative to the second purified psilocybin derivative.

In one embodiment, the compositions disclosed herein comprise a molar ratio between about 100:1 to about 1:100 of the first purified psilocybin derivative to the second purified psilocybin derivative.

In one embodiment, the compositions disclosed herein comprise a molar ratio between about 1,000:1 to about 1:1,000 of the first purified psilocybin derivative to the second purified psilocybin derivative.

In one embodiment, the compositions disclosed herein comprise a molar ratio of about 10,000:1 to about 1:10,000 of the first purified psilocybin derivative to the second purified psilocybin derivative.

In one embodiment, the first purified psilocybin derivative is [3-(2-Dimethylaminoethyl)-1H-indol-4-yl] dihydrogen phosphate.

In one embodiment, the first purified psilocybin derivative is 4-hydroxy-N,N-dimethyltryptamine.

In one embodiment, the first purified psilocybin derivative is [3-(2-methylaminoethyl)-1H-indol-4-yl] dihydrogen phosphate.

In one embodiment, the first purified psilocybin derivative is 4-hydroxy-N-methyltryptamine.

In one embodiment, the first purified psilocybin derivative is [3-(aminoethyl)-1H-indol-4-yl] dihydrogen phosphate.

In one embodiment, the first purified psilocybin derivative is 4-hydroxytryptamine.

In one embodiment, the first purified psilocybin derivative is [3-(2-trimethylaminoethyl)-1H-indol-4-yl] dihydrogen phosphate.

In one embodiment, the first purified psilocybin derivative is 4-hydroxy-N,N,N-trimethyltryptamine.

As used herein, the term "psilocybin derivative" refers to a compound having a core structure similar to the compound [3-(2-Dimethylaminoethyl)-1H-indol-4-yl] dihydrogen phosphate, aka "psilocybin". In one embodiment, a psilocybin derivative is dephosphorylated, such as a phenol or derivative thereof. In one embodiment, a psilocybin derivative comprises zero, one, two, or three alkyl groups covalently bonded to the nitrogen atom on the aminoethyl group. In one embodiment, a psilocybin derivative comprises an amine ($-NH_2$) group. In one embodiment, a psilocybin derivative comprises a hydroxyl ($-OH$) group. In one embodiment, a psilocybin derivative comprises a carbonyl group. In one embodiment, a psilocybin derivative comprises an ester group. In one embodiment, a psilocybin derivative comprises a carboxyl group. In one embodiment, a psilocybin derivative comprises an amide group.

In one embodiment, a psilocybin derivative within the compositions disclosed herein is a compound defined by the following structural formula A:

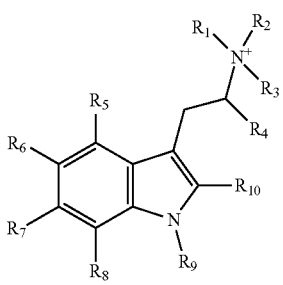

wherein each of $R_1$, $R_2$, $R_3$, $R_4$, $R_5$, $R_6$, $R_7$, $R_8$, $R_9$, and $R_{10}$ is chosen from an electron pair, a hydrogen, an alkyl, an alkenyl, an alkynyl, a phenyl, a halide, a hydroxyl, a carbonyl, an aldehyde, a haloformyl, a carbonate ester, a carboxylate, a carboxyl, an ester, a hydroperoxy, a peroxy, an ether, a hemiacetal, a hemiketal, an acetal, a ketal, an orthoester, a methylenedioxy, an orthocarbonate ester, carboxamide, an amine, an imine, an amide, an azide, an azo, a cyanate, a nitrate, a nitrile, an isonitrile, a nitrosooxy, a nitro, a pyridyl, a thiol, a sulfide, sulfinyl, a sulfonyl, a thiocyanate, a carbonothioyl, or a phosphate.

In one embodiment, a psilocybin derivative is a compound defined by the structural formula A, wherein each of $R_1$, $R_2$, and $R_3$ is independently chosen from an electron pair, a hydrogen, or an alkyl; wherein $R_4$ is hydrogen; wherein $R_5$ is chosen from a hydroxyl, an ether, or a phosphate; and wherein each of $R_6$ $R_7$, $R_8$, $R_9$, and $R_{10}$ is hydrogen.

In one embodiment, a psilocybin derivative is a compound defined by the structural formula A, wherein each of $R_1$, $R_2$, and $R_3$ is independently chosen from an electron pair, a hydrogen, or an alkyl; wherein each of $R_4$ and $R_5$ is hydrogen; wherein $R_6$ is chosen from a hydroxyl, an ether, or a phosphate; and wherein each of $R_7$, $R_8$, $R_9$, and $R_{10}$ is hydrogen.

In one embodiment, a "first psilocybin derivative" is [3-(2-Dimethylaminoethyl)-1H-indol-4-yl] dihydrogen phosphate.

As used herein, the term "[3-(2-Dimethylaminoethyl)-1H-indol-4-yl] dihydrogen phosphate" refers to a compound, and/or salts thereof, with the following structural formula:

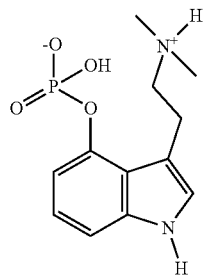

[3-(2-Dimethylaminoethyl)-1H-indol-4-yl] dihydrogen phosphate is often described by the name "psilocybin". Psilocybin is a psychoactive prodrug often found in mushrooms of genus *Psilocybe*. See American Chemical Society, Molecule of the Week (Oct. 2, 2017). When ingested, psilocybin is converted into psilocin through chemical and/or biological processes in the human body. Id. Within the context of this disclosure, unless otherwise specified, [3-(2-Dimethylaminoethyl)-1H-indol-4-yl] dihydrogen phosphate may be present in its protonated or deprotonated (salt or freebase) forms or mixtures thereof depending on the context, for example the pH of the solution or composition.

In one embodiment, a "first psilocybin derivative" is 4-hydroxy-N,N-dimethyltryptamine.

As used herein, the term "4-hydroxy-N,N-dimethyltryptamine" refers to a compound, and/or salts thereof, with the following structural formula:

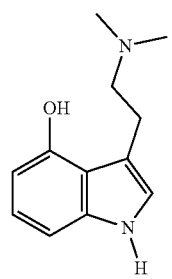

4-hydroxy-N,N-dimethyltryptamine is also known by the name "psilocin". Within the context of this disclosure, unless otherwise specified, 4-hydroxy-N,N-dimethyltryptamine may be present in its protonated or deprotonated (salt or freebase) forms or mixtures thereof depending on the context, for example the pH of the solution or composition.

In one embodiment, a "first psilocybin derivative" is [3-(2-trimethylaminoethyl)-1H-indol-4-yl] dihydrogen phosphate.

As used herein, the term "[3-(2-trimethylaminoethyl)-1H-indol-4-yl] dihydrogen phosphate" refers to a compound, and/or salts thereof, with the following structural formula:

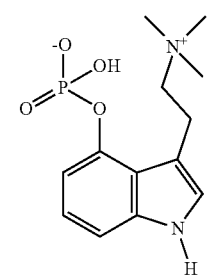

Within the context of this disclosure, unless otherwise specified, [3-(2-trimethylaminoethyl)-1H-indol-4-yl] dihydrogen phosphate may be present in its protonated or deprotonated (salt or freebase) forms or mixtures thereof depending on the context, for example the pH of the solution or composition.

In one embodiment, a "first psilocybin derivative" is 4-hydroxy-N,N,N-trimethyltryptamine.

As used herein, the term "4-hydroxy-N,N,N-trimethyltryptamine" refers to a compound, and/or salts thereof, with the following structural formula:

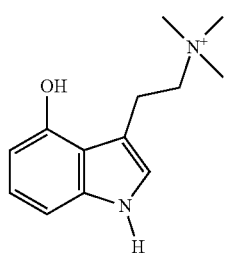 [SMILES: C[N+](C)(C)CCc1c[nH]c2cccc(O)c12]

Within the context of this disclosure, unless otherwise specified, 4-hydroxy-N,N,N-trimethyltryptamine may be present in its protonated or deprotonated (salt or freebase) forms or mixtures thereof depending on the context, for example the pH of the solution or composition.

In one embodiment, a "first psilocybin derivative" is [3-(2-methylaminoethyl)-1H-indol-4-yl] dihydrogen phosphate.

As used herein, the term "[3-(2-methylaminoethyl)-1H-indol-4-yl] dihydrogen phosphate" refers to a compound, and/or salts thereof, with the following structural formula:

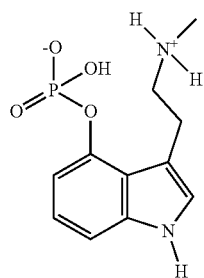

Within the context of this disclosure, unless otherwise specified, [3-(2-methylaminoethyl)-1H-indol-4-yl] dihydrogen phosphate may be present in its protonated or deprotonated (salt or freebase) forms or mixtures thereof depending on the context, for example the pH of the solution or composition.

In one embodiment, a "first psilocybin derivative" is 4-hydroxy-N-methyltryptamine.

As used herein, the term "4-hydroxy-N-methyltryptamine" refers to a compound, and/or salts thereof, with the following structural formula:

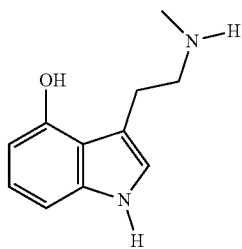

Within the context of this disclosure, unless otherwise specified, 4-hydroxy-N-methyltryptamine may be present in its protonated or deprotonated (salt or freebase) forms or mixtures thereof depending on the context, for example the pH of the solution or composition.

In one embodiment, a "first psilocybin derivative" is [3-(aminoethyl)-1H-indol-4-yl] dihydrogen phosphate.

As used herein, the term "[3-(aminoethyl)-1H-indol-4-yl] dihydrogen phosphate" refers to a compound, and/or salts thereof, with the following structural formula:

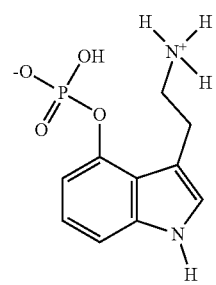

Within the context of this disclosure, unless otherwise specified, [3-(aminoethyl)-1H-indol-4-yl] dihydrogen phosphate may be present in its protonated or deprotonated (salt or freebase) forms or mixtures thereof depending on the context, for example the pH of the solution or composition.

In one embodiment, a "first psilocybin derivative" is 4-hydroxytryptamine.

As used herein, the term "4-hydroxytryptamine" refers to a compound, and/or salts thereof, with the following structural formula:

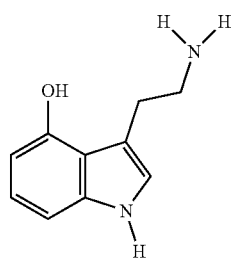 [SMILES: NCCc1c[nH]c2cccc(O)c12]

Within the context of this disclosure, unless otherwise specified, 4-hydroxytryptamine may be present in its protonated or deprotonated (salt or freebase) forms or mixtures thereof depending on the context, for example the pH of the solution or composition.

As used herein, the term "salt" refers to a neutralized ionic compound. In one embodiment, a salt is formed from the neutralization of acids and bases. In one embodiment, a salt is electrically neutral.

In one embodiment, the compositions and methods disclosed herein comprise administering a first cannabinoid. In one embodiment, a first cannabinoid is a first purified cannabinoid.

As used herein, the term "cannabinoid" refers to a compound from a class of molecules commonly found in plants of the genus *cannabis* and their derivatives. In one embodiment, the cannabinoid is endogenous to an animal, i.e., an endocannabinoid. In one embodiment, the cannabinoid is derived from a plant, e.g., a plant of genus *cannabis*, i.e., a phytocannabinoid. In one embodiment, the cannabinoid is artificially made in a lab, i.e., a synthetic cannabinoid. Many cannabinoids can be identified by the "cannabi" text in their chemical name. There are at least 113 different cannabinoids isolated from *cannabis*, exhibiting varied (similar and different) effects.

Examples of cannabinoids within the context of this disclosure include the following molecules: Cannabichromene (CBC), Cannabichromenic acid (CBCA), Cannabichromevarin (CBCV), Cannabichromevarinic acid (CBCVA), Cannabicyclol (CBL), Cannabicyclolic acid (CBLA), Cannabicyclovarin (CBLV), Cannabidiol (CBD), Cannabidiol monomethylether (CBDM), Cannabidiolic acid (CBDA), Cannabidiorcol (CBD-C1), Cannabidivarin (CBDV), Cannabidivarinic acid (CBDVA), Cannabielsoic acid B (CBEA-B), Cannabielsoin (CBE), Cannabielsoin acid A (CBEA-A), Cannabigerol (CBG), Cannabigerol monomethylether (CBGM), Cannabigerolic acid (CBGA), Cannabigerolic acid monomethylether (CBGAM), Cannabigerovarin (CBGV), Cannabigerovarinic acid (CBGVA), Cannabinodiol (CBND), Cannabinodivarin (CBDV), Cannabinol (CBN), Cannabinol methylether (CBNM), Cannabinol-C2 (CBN-C2), Cannabinol-C4 (CBN-C4), Cannabinolic acid (CBNA), Cannabiorcool (CBN-C1), Cannabivarin (CBV), Cannabitriol (CBT), Cannabitriolvarin (CBTV), 10-Ethoxy-9-hydroxy-delta-6a-tetrahydrocannabinol, Cannbicitran (CBT), Cannabiripsol (CBR), 8,9-Dihydroxy-delta-6a-tetrahydrocannabinol, Delta-8-tetrahydrocannabinol (Δ8-THC), Delta-8-tetrahydrocannabinolic acid (Δ8-THCA), Delta-9-tetrahydrocannabinol (THC), Delta-9-tetrahydrocannabinol-C4 (THC-C4), Delta-9-tetrahydrocannabinolic acid A (THCA-A), Delta-9-tetrahydrocannabinolic acid B (THCA-B), Delta-9-tetrahydrocannabinolic acid-C4 (THCA-C4), Delta-9-tetrahydrocannabiorcol (THC-C1), Delta-9-tetrahydrocannabiorcolic acid (THCA-C1), Delta-9-tetrahydrocannabivarin (THCV), Delta-9-tetrahydrocannabivarinic acid (THCVA), 10-Oxo-delta-6a-tetrahydrocannabinol (OTHC), Cannabichromanon (CBCF), Cannabifuran (CBF), Cannabiglendol, Delta-9-cis-tetrahydrocannabinol (cis-THC), Tryhydroxy-delta-9-tetrahydrocannabinol (triOH-THC), Dehydrocannabifuran (DCBF), and 3,4,5,6-Tetrahydro-7-hydroxy-alpha-alpha-2-trimethyl-9-n-propyl-2,6-methano-2H-1-benzoxocin-5-methanol.

In one embodiment, the term "cannabinoid" refers to a compound chosen from THC, THCA, THCV, THCVA, CBC, CBCA, CBCV, CBCVA, CBD, CBDA, CBDV, CBDVA, CBG, CBGA, CBGV, or CBGVA.

As used herein, the term "THC", or tetrahydrocannabinol, refers to a compound with the following structural formula:

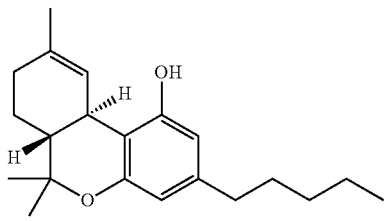 [SMILES: CCCCCc1cc(O)c2c(c1)OC(C)(C)[C@@H]1CCC(C)=C[C@@H]21]

Within the context of this disclosure, the term "THC" comprises any derivative and/or salt thereof. In one embodiment, the compositions and methods disclosed herein comprise administering a formulation of THC and a first psilocybin derivative. In one embodiment, the compositions and methods disclosed herein comprise administering purified THC and a first psilocybin derivative. In one embodiment, the compositions and methods disclosed herein comprise administering THC and a first purified psilocybin derivative. In one embodiment, the compositions and methods disclosed herein comprise administering purified THC and a first purified psilocybin derivative.

As used herein, the term "THCA" refers to a compound with the following structural formula:

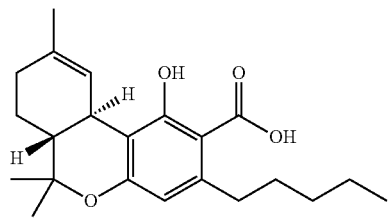 [SMILES: CCCCCc1cc2c(c(O)c1C(=O)O)[C@@H]1C=C(C)CC[C@H]1C(C)(C)O2]

Within the context of this disclosure, the term "THCA" comprises any derivative and/or salt thereof. In one embodiment, the compositions and methods disclosed herein comprise administering a formulation of THCA and a first psilocybin derivative. In one embodiment, the compositions and methods disclosed herein comprise administering purified THCA and a first psilocybin derivative. In one embodiment, the compositions and methods disclosed herein comprise administering THCA and a first purified psilocybin derivative. In one embodiment, the compositions and methods disclosed herein comprise administering purified THCA and a first purified psilocybin derivative.

As used herein, the term "THCV" refers to a compound with the following structural formula:

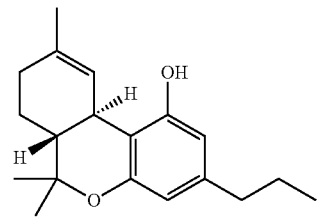 [SMILES: CCCc1cc(O)c2c(c1)OC(C)(C)[C@@H]1CCC(C)=C[C@@H]21]

Within the context of this disclosure, the term "THCV" comprises any derivative and/or salt thereof. In one embodiment, the compositions and methods disclosed herein comprise administering a formulation of THCV and a first psilocybin derivative. In one embodiment, the compositions and methods disclosed herein comprise administering purified THCV and a first psilocybin derivative. In one embodiment, the compositions and methods disclosed herein comprise administering THCV and a first purified psilocybin derivative. In one embodiment, the compositions and methods disclosed herein comprise administering purified THCV and a first purified psilocybin derivative.

As used herein, the term "THCVA" refers to a compound with the following structural formula:

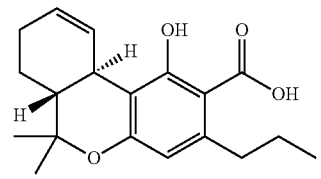 [SMILES: CCCc1cc2c(c(O)c1C(=O)O)[C@@H]1C=CCC[C@H]1C(C)(C)O2]

Within the context of this disclosure, the term "THCVA" comprises any derivative and/or salt thereof. In one embodiment, the compositions and methods disclosed herein comprise administering a formulation of THCVA and a first psilocybin derivative. In one embodiment, the compositions and methods disclosed herein comprise administering purified THCVA and a first psilocybin derivative. In one embodiment, the compositions and methods disclosed herein comprise administering THCVA and a first purified psilocybin derivative. In one embodiment, the compositions and methods disclosed herein comprise administering purified THCVA and a first purified psilocybin derivative.

As used herein, the term "CBC" refers to a compound with the following structural formula:

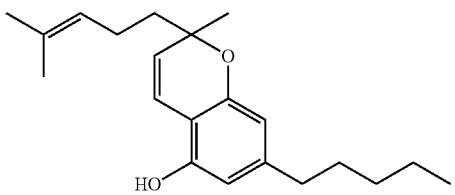 [SMILES: CCCCCc1cc(O)c2c(c1)OC(C)(CCC=C(C)C)C=C2]

Within the context of this disclosure, the term "CBC" comprises any derivative and/or salt thereof. In one embodiment, the compositions and methods disclosed herein comprise administering a formulation of CBC and a first psilocybin derivative. In one embodiment, the compositions and methods disclosed herein comprise administering purified CBC and a first psilocybin derivative. In one embodiment, the compositions and methods disclosed herein comprise administering CBC and a first purified psilocybin derivative. In one embodiment, the compositions and methods disclosed herein comprise administering purified CBC and a first purified psilocybin derivative.

As used herein, the term "CBCA" refers to a compound with the following structural formula:

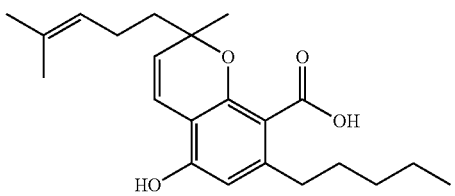 [SMILES: CCCCCc1cc(O)c2c(c1C(=O)O)OC(C)(CCC=C(C)C)C=C2]

Within the context of this disclosure, the term "CBCA" comprises any derivative and/or salt thereof. In one embodiment, the compositions and methods disclosed herein comprise administering a formulation of CBCA and a first psilocybin derivative. In one embodiment, the compositions and methods disclosed herein comprise administering purified CBCA and a first psilocybin derivative. In one embodiment, the compositions and methods disclosed herein comprise administering CBCA and a first purified psilocybin derivative. In one embodiment, the compositions and methods disclosed herein comprise administering purified CBCA and a first purified psilocybin derivative.

As used herein, the term "CBCV" refers to a compound with the following structural formula:

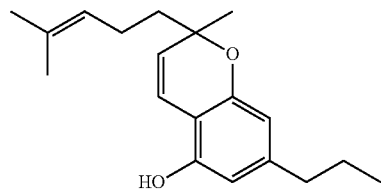 [SMILES: CCCc1cc(O)c2c(c1)OC(C)(CCC=C(C)C)C=C2]

Within the context of this disclosure, the term "CBCV" comprises any derivative and/or salt thereof. In one embodiment, the compositions and methods disclosed herein comprise administering a formulation of CBCV and a first psilocybin derivative. In one embodiment, the compositions and methods disclosed herein comprise administering purified CBCV and a first psilocybin derivative. In one embodiment, the compositions and methods disclosed herein comprise administering CBCV and a first purified psilocybin derivative. In one embodiment, the compositions and methods disclosed herein comprise administering purified CBCV and a first purified psilocybin derivative.

As used herein, the term "CBCVA" refers to a compound with the following structural formula:

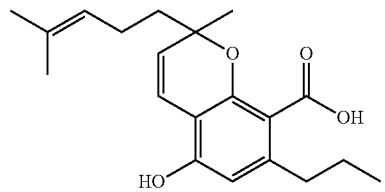 [SMILES: CCCc1cc(O)c2c(c1C(=O)O)OC(C)(CCC=C(C)C)C=C2]

Within the context of this disclosure, the term "CBCVA" comprises any derivative and/or salt thereof. In one embodiment, the compositions and methods disclosed herein comprise administering a formulation of CBCVA and a first psilocybin derivative. In one embodiment, the compositions and methods disclosed herein comprise administering purified CBCVA and a first psilocybin derivative. In one embodiment, the compositions and methods disclosed herein comprise administering CBCVA and a first purified psilocybin derivative. In one embodiment, the compositions and methods disclosed herein comprise administering purified CBCVA and a first purified psilocybin derivative.

As used herein, the term "CBD" refers to a compound with the following structural formula:

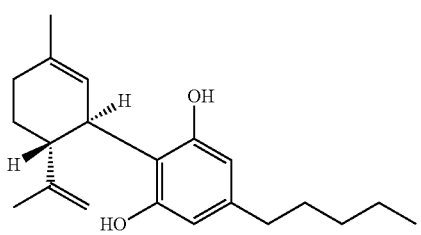 [SMILES: C=C(C)[C@@H]1CCC(C)=C[C@H]1c1c(O)cc(CCCCC)cc1O]

Within the context of this disclosure, the term "CBD" comprises any derivative and/or salt thereof. In one embodiment, the compositions and methods disclosed herein comprise administering a formulation of CBD and a first psilocybin derivative. In one embodiment, the compositions and methods disclosed herein comprise administering purified CBD and a first psilocybin derivative. In one embodiment, the compositions and methods disclosed herein comprise administering CBD and a first purified psilocybin derivative. In one embodiment, the compositions and methods disclosed herein comprise administering purified CBD and a first purified psilocybin derivative.

As used herein, the term "CBDA" refers to a compound with the following structural formula:

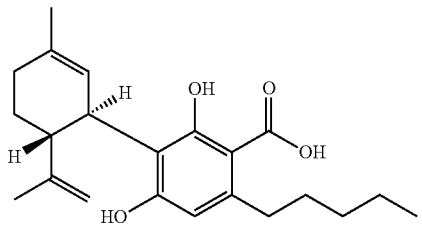 [SMILES: C=C(C)[C@@H]1CCC(C)=C[C@H]1c1c(O)cc(CCCCC)c(C(=O)O)c1O]

Within the context of this disclosure, the term "CBDA" comprises any derivative and/or salt thereof. In one embodiment, the compositions and methods disclosed herein comprise administering a formulation of CBDA and a first psilocybin derivative. In one embodiment, the compositions and methods disclosed herein comprise administering purified CBDA and a first psilocybin derivative. In one embodiment, the compositions and methods disclosed herein comprise administering CBDA and a first purified psilocybin derivative. In one embodiment, the compositions and methods disclosed herein comprise administering purified CBDA and a first purified psilocybin derivative.

As used herein, the term "CBDV" refers to a compound with the following structural formula:

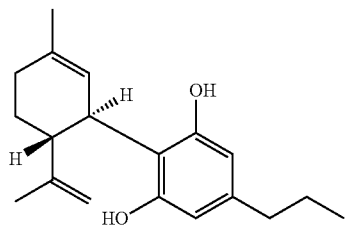 [SMILES: C=C(C)[C@@H]1CCC(C)=C[C@H]1c1c(O)cc(CCC)cc1O]

Within the context of this disclosure, the term "CBDV" comprises any derivative and/or salt thereof. In one embodiment, the compositions and methods disclosed herein comprise administering a formulation of CBDV and a first psilocybin derivative. In one embodiment, the compositions and methods disclosed herein comprise administering purified CBDV and a first psilocybin derivative. In one embodiment, the compositions and methods disclosed herein comprise administering CBDV and a first purified psilocybin derivative. In one embodiment, the compositions and methods disclosed herein comprise administering purified CBDV and a first purified psilocybin derivative.

As used herein, the term "CBDVA" refers to a compound with the following structural formula:

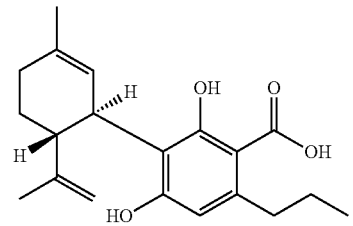 [SMILES: C=C(C)[C@@H]1CCC(C)=C[C@H]1c1c(O)cc(CCC)c(C(=O)O)c1O]

Within the context of this disclosure, the term "CBDVA" comprises any derivative and/or salt thereof. In one embodiment, the compositions and methods disclosed herein comprise administering a formulation of CBDVA and a first psilocybin derivative. In one embodiment, the compositions and methods disclosed herein comprise administering purified CBDVA and a first psilocybin derivative. In one embodiment, the compositions and methods disclosed herein comprise administering CBDVA and a first purified psilocybin derivative. In one embodiment, the compositions and methods disclosed herein comprise administering purified CBDVA and a first purified psilocybin derivative.

As used herein, the term "CBG" refers to a compound with the following structural formula:

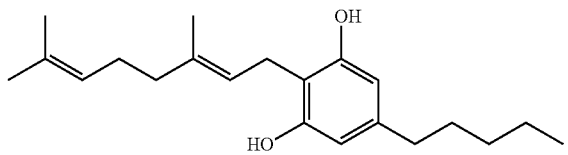 [SMILES: CCCCCc1cc(O)c(C/C=C(\C)CCC=C(C)C)c(O)c1]

Within the context of this disclosure, the term "CBG" comprises any derivative and/or salt thereof. In one embodiment, the compositions and methods disclosed herein comprise administering a formulation of CBG and a first psilocybin derivative. In one embodiment, the compositions and methods disclosed herein comprise administering purified CBG and a first psilocybin derivative. In one embodiment, the compositions and methods disclosed herein comprise administering CBG and a first purified psilocybin derivative. In one embodiment, the compositions and methods disclosed herein comprise administering purified CBG and a first purified psilocybin derivative.

As used herein, the term "CBGA" refers to a compound with the following structural formula:

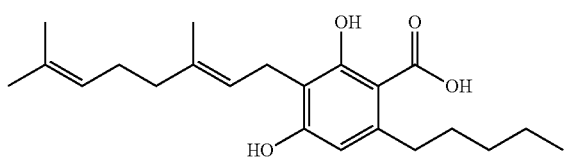 [SMILES: CCCCCc1cc(O)c(C/C=C(\C)CCC=C(C)C)c(O)c1C(=O)O]

Within the context of this disclosure, the term "CBGA" comprises any derivative and/or salt thereof. In one embodiment, the compositions and methods disclosed herein comprise administering a formulation of CBGA and a first psilocybin derivative. In one embodiment, the compositions and methods disclosed herein comprise administering purified CBGA and a first psilocybin derivative. In one embodiment, the compositions and methods disclosed herein comprise administering CBGA and a first purified psilocybin derivative. In one embodiment, the compositions and methods disclosed herein comprise administering purified CBGA and a first purified psilocybin derivative.

As used herein, the term "CBGV" refers to a compound with the following structural formula:

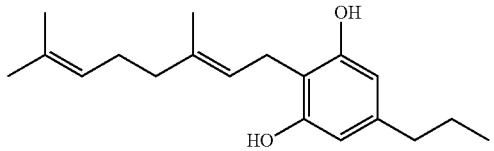 [SMILES: CCCc1cc(O)c(C/C=C(\C)CCC=C(C)C)c(O)c1]

Within the context of this disclosure, the term "CBGV" comprises any derivative and/or salt thereof. In one embodiment, the compositions and methods disclosed herein comprise administering a formulation of CBGV and a first psilocybin derivative. In one embodiment, the compositions and methods disclosed herein comprise administering purified CBGV and a first psilocybin derivative. In one embodiment, the compositions and methods disclosed herein comprise administering CBGV and a first purified psilocybin derivative. In one embodiment, the compositions and methods disclosed herein comprise administering purified CBGV and a first purified psilocybin derivative.

As used herein, the term "CBGVA" refers to a compound with the following structural formula:

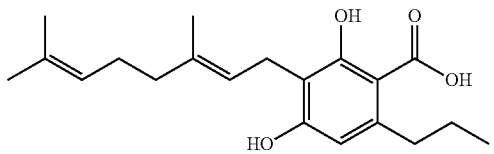 [SMILES: CCCc1cc(O)c(C/C=C(\C)CCC=C(C)C)c(O)c1C(=O)O]

Within the context of this disclosure, the term "CBGVA" comprises any derivative and/or salt thereof. In one embodiment, the compositions and methods disclosed herein comprise administering a formulation of CBGVA and a first psilocybin derivative. In one embodiment, the compositions and methods disclosed herein comprise administering purified CBGVA and a first psilocybin derivative. In one embodiment, the compositions and methods disclosed herein comprise administering CBGVA and a first purified psilocybin derivative. In one embodiment, the compositions and methods disclosed herein comprise administering purified CBGVA and a first purified psilocybin derivative.

In one embodiment, the compositions disclosed herein comprise a particular ratio (e.g., a molar ratio) between about 100:1 to about 1:100 of the first purified psilocybin derivative and the first purified cannabinoid.

In one embodiment, the compositions disclosed herein comprise a particular ratio (e.g., a molar ratio) between about 75:1 to about 1:75 of the first purified psilocybin derivative and the first purified cannabinoid.

In one embodiment, the compositions disclosed herein comprise a particular ratio (e.g., a molar ratio) between about 50:1 to about 1:50 of the first purified psilocybin derivative and the first purified cannabinoid.

In one embodiment, the compositions disclosed herein comprise a particular ratio (e.g., a molar ratio) between about 25:1 to about 1:25 of the first purified psilocybin derivative and the first purified cannabinoid.

In one embodiment, the compositions disclosed herein comprise a particular ratio (e.g., a molar ratio) between about 10:1 to about 1:10 of the first purified psilocybin derivative and the first purified cannabinoid.

In one embodiment, the compositions disclosed herein comprise a particular ratio (e.g., a molar ratio) between about 5:1 to about 1:5 of the first purified psilocybin derivative and the first purified cannabinoid.

In one embodiment, the compositions and methods disclosed herein comprise a first purified psilocybin derivative, a first purified cannabinoid, and a second purified cannabinoid.

In one embodiment, the second purified cannabinoid is chosen from THC, THCA, THCV, THCVA, CBC, CBCA, CBCV, CBCVA, CBD, CBDA, CBDV, CBDVA, CBG, CBGA, CBGV, or CBGVA.

In one embodiment, the compositions disclosed herein comprise a particular ratio (e.g., a molar ratio) between about 100:1 to about 1:100 of the first purified psilocybin derivative and the sum of the first purified cannabinoid and the second purified cannabinoid.

In one embodiment, the compositions disclosed herein comprise a particular ratio (e.g., a molar ratio) between about 75:1 to about 1:75 of the first purified psilocybin derivative and the sum of the first purified cannabinoid and the second purified cannabinoid.

In one embodiment, the compositions disclosed herein comprise a particular ratio (e.g., a molar ratio) between about 50:1 to about 1:50 of the first purified psilocybin derivative and the sum of the first purified cannabinoid and the second purified cannabinoid.

In one embodiment, the compositions disclosed herein comprise a particular ratio (e.g., a molar ratio) between about 25:1 to about 1:25 of the first purified psilocybin derivative and the sum of the first purified cannabinoid and the second purified cannabinoid.

In one embodiment, the compositions disclosed herein comprise a particular ratio (e.g., a molar ratio) between about 10:1 to about 1:10 of the first purified psilocybin derivative and the sum of the first purified cannabinoid and the second purified cannabinoid.

In one embodiment, the compositions disclosed herein comprise a particular ratio (e.g., a molar ratio) between about 5:1 to about 1:5 of the first purified psilocybin derivative and the sum of the first purified cannabinoid and the second purified cannabinoid.

In one embodiment, the compositions and methods disclosed herein comprise administering a first terpene. In one embodiment, the first terpene is a first purified terpene.

As used herein, the term "terpene" refers to a compound belonging to a large class of compounds often biosynthesized from 5-carbon isoprene units. In one embodiment, a terpene is produced by a variety of plants, e.g., conifers, *cannabis*, basil, etc. In one embodiment, a terpene is produced by an insect, e.g., termites or swallowtail butterflies. In one embodiment, a terpene is a volatile compound. In one embodiment, a terpene produces an odor. In one embodiment, a terpene is a major component of a natural resin, e.g., turpentine produced from resin. In one embodiment, a terpene is derived biosynthetically from units of isoprene, which has the molecular formula $C_5H_8$. In one embodiment, the molecular formula of terpenes are multiples of $(C_5H_8)_n$, where n is the number of linked isoprene units.

Within the context of this disclosure when a terpene is modified chemically, such as by oxidation or rearrangement of the carbon skeleton, the resulting compound is referred to as a terpenoid. In the relevant arts, terpenoids are sometimes referred to as isoprenoids.

In one embodiment, a terpene is the primary constituent or constituents of an essential oil from a plant and/or flower. Essential oils are used widely as fragrances in perfumery, medicine, and alternative medicines, e.g., aromatherapy.

In one embodiment, a terpene is categorized according to the number of isoprene ($C_5H_8$) units in the compound, for example a monoterpene ($C_{10}H_{16}$), a sesquiterpene ($C_{15}H_{24}$), a diterpene ($C_{20}H_{32}$), a triterpene ($C_{30}H_{48}$), or a tetraterpene ($C_{40}H_{64}$).

In one embodiment, a first purified terpene is chosen from acetanisole, acetyl cedrene, anethole, anisole, benzaldehyde, bornyl acetate, borneol, cadinene, cafestol, caffeic acid, camphene, camphor, capsaicin, carene, carotene, carvacrol, carvone, alpha-caryophyllene, beta-caryophyllene, caryophyllene oxide, cedrene, cedrene epoxide, cecanal, cedrol, cembrene, cinnamaldehyde, cinnamic acid, citronellal, citronellol, cymene, eicosane, elemene, estragole, ethyl acetate, ethyl cinnamate, ethyl maltol, eucalyptol/1,8-cineole, eudesmol, eugenol, euphol, farnesene, farnesol, fenchone, geraniol, geranyl acetate, guaia-1(10),11-diene, guaiacol, guaiol, guaiene, gurjunene, herniarin, hexanaldehyde, hexanoic acid, humulene, ionone, ipsdienol, isoamyl acetate, isoamyl alcohol, isoamyl formate, isoborneol, isomyrcenol, isoprene, isopulegol, isovaleric acid, lavandulol, limonene, gamma-linolenic acid, linalool, longifolene, lycopene, menthol, methyl butyrate, 3-mercapto-2-methylpentanal, beta-mercaptoethanol, mercaptoacetic acid, methyl salicylate, methylbutenol, methyl-2-methylvalerate, methyl thiobutyrate, beta-myrcene, gamma-muurolene, nepetalactone, nerol, nerolidol, neryl acetate, nonanaldehyde, nonanoic acid, ocimene, octanal, octanoic acid, pentyl butyrate, phellandrene, phenylacetaldehyde, phenylacetic acid, phenylethanethiol, phytol, pinene, propanethiol, pristimerin, pulegone, retinol, rutin, sabinene, squalene, taxadiene, terpineol, terpine-4-ol, terpinolene, thujone, thymol, umbelliferone, undecanal, verdoxan, or vanillin.

In one embodiment, a first purified terpene is chosen from bornyl acetate, alpha-bisabolol, borneol, camphene, camphor, carene, beta-caryophyllene, cedrene, cymene, elemene, eucalyptol, eudesmol, farnesene, fenchol, geraniol, guaiacol, humulene, isoborneol, limonene, linalool, menthol, beta-myrcene, nerolidol, ocimene, phellandrene, phytol, pinene, pulegone, sabinene, terpineol, terpinolene, or valencene.

As used herein, the term "bornyl acetate" refers to a compound with the following structural formula:

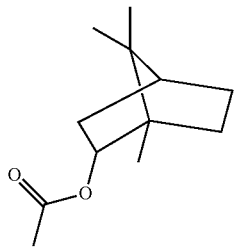

Within the context of this disclosure, the term "bornyl acetate" comprises any derivative and/or salt thereof, including any isomeric, structural and/or enantiomeric, variations thereof. In one embodiment, the compositions and methods disclosed herein comprise administering a formulation of bornyl acetate and a first psilocybin derivative. In one embodiment, the compositions and methods disclosed herein comprise administering a formulation of purified bornyl acetate and a first psilocybin derivative. In one embodiment, the compositions and methods disclosed herein comprise administering a formulation of bornyl acetate and a first purified psilocybin derivative. In one embodiment, the compositions and methods disclosed herein comprise administering a formulation of purified bornyl acetate and a first purified psilocybin derivative.

As used herein, the term "alpha-bisabolol" refers to a compound with the following structural formula:

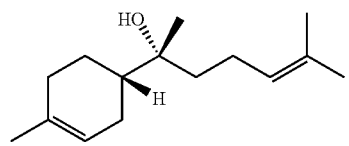 [SMILES: CC(C)=CCC[C@@](C)(O)[C@@H]1CC=C(C)CC1]

Within the context of this disclosure, the term "alpha-bisabolol" comprises any derivative and/or salt thereof, including any isomeric, structural and/or enantiomeric, variations thereof. In one embodiment, the compositions and methods disclosed herein comprise administering a formulation of alpha-bisabolol and a first psilocybin derivative. In one embodiment, the compositions and methods disclosed herein comprise administering a formulation of purified alpha-bisabolol and a first psilocybin derivative. In one embodiment, the compositions and methods disclosed herein comprise administering a formulation of alpha-bisabolol and a first purified psilocybin derivative. In one embodiment, the compositions and methods disclosed herein comprise administering a formulation of purified alpha-bisabolol and a first purified psilocybin derivative.

As used herein, the term "borneol" refers to a compound with the following structural formula:

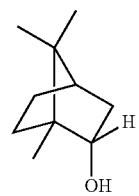

Within the context of this disclosure, the term "borneol" comprises any derivative and/or salt thereof, including any isomeric, structural and/or enantiomeric, variations thereof. In one embodiment, the compositions and methods disclosed herein comprise administering a formulation of borneol and a first psilocybin derivative. In one embodiment, the compositions and methods disclosed herein comprise administering a formulation of purified borneol and a first psilocybin derivative. In one embodiment, the compositions and methods disclosed herein comprise administering a formulation of borneol and a first purified psilocybin derivative. In one embodiment, the compositions and methods disclosed herein comprise administering a formulation of purified borneol and a first purified psilocybin derivative.

As used herein, the term "camphene" refers to a compound with the following structural formula:

Within the context of this disclosure, the term "camphene" comprises any derivative and/or salt thereof, including any isomeric, structural and/or enantiomeric, variations thereof. In one embodiment, the compositions and methods disclosed herein comprise administering a formulation of camphene and a first psilocybin derivative. In one embodiment, the compositions and methods disclosed herein comprise administering a formulation of purified camphene and a first psilocybin derivative. In one embodiment, the compositions and methods disclosed herein comprise administering a formulation of camphene and a first purified psilocybin derivative. In one embodiment, the compositions and methods disclosed herein comprise administering a formulation of purified camphene and a first purified psilocybin derivative.

As used herein, the term "camphor" refers to a compound with either of the following structural formulas:

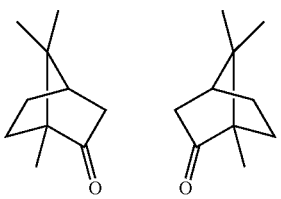

Within the context of this disclosure, the term "camphor" comprises any derivative and/or salt thereof, including any isomeric, structural and/or enantiomeric, variations thereof. In one embodiment, the compositions and methods disclosed herein comprise administering a formulation of camphor and a first psilocybin derivative. In one embodiment, the compositions and methods disclosed herein comprise administering a formulation of purified camphor and a first psilocybin derivative. In one embodiment, the compositions and methods disclosed herein comprise administering a formulation of camphor and a first purified psilocybin derivative. In one embodiment, the compositions and methods disclosed herein comprise administering a formulation of purified camphor and a first purified psilocybin derivative.

As used herein, the term "carene" refers to a compound with the following structural formula:

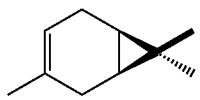

Within the context of this disclosure, the term "carene" comprises any derivative and/or salt thereof, including any isomeric, structural and/or enantiomeric, variations thereof. In one embodiment, the compositions and methods disclosed herein comprise administering a formulation of carene and a first psilocybin derivative. In one embodiment, the compositions and methods disclosed herein comprise administering a formulation of purified carene and a first psilocybin derivative. In one embodiment, the compositions and methods disclosed herein comprise administering a formulation of carene and a first purified psilocybin derivative. In one embodiment, the compositions and methods disclosed herein comprise administering a formulation of purified carene and a first purified psilocybin derivative.

As used herein, the term "beta-caryophyllene" refers to a compound with the following structural formula:

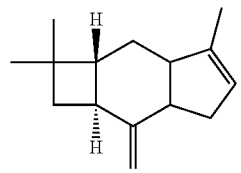

Within the context of this disclosure, the term "beta-caryophyllene" comprises any derivative and/or salt thereof, including any isomeric, structural and/or enantiomeric, variations thereof. In one embodiment, the compositions and methods disclosed herein comprise administering a formulation of beta-caryophyllene and a first psilocybin derivative. In one embodiment, the compositions and methods disclosed herein comprise administering a formulation of purified beta-caryophyllene and a first psilocybin derivative. In one embodiment, the compositions and methods disclosed herein comprise administering a formulation of beta-caryophyllene and a first purified psilocybin derivative. In one embodiment, the compositions and methods disclosed herein comprise administering a formulation of purified beta-caryophyllene and a first purified psilocybin derivative.

As used herein, the term "cedrene" refers to a compound with either of the following structural formulas:

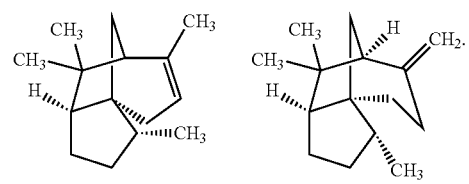

Within the context of this disclosure, the term "cedrene" comprises any derivative and/or salt thereof, including any isomeric, structural and/or enantiomeric, variations thereof. In one embodiment, the compositions and methods disclosed herein comprise administering a formulation of cedrene and a first psilocybin derivative. In one embodiment, the compositions and methods disclosed herein comprise administering a formulation of purified cedrene and a first psilocybin derivative. In one embodiment, the compositions and methods disclosed herein comprise administering a formulation of cedrene and a first purified psilocybin derivative. In one embodiment, the compositions and methods disclosed herein comprise administering a formulation of purified cedrene and a first purified psilocybin derivative.

As used herein, the term "cymene" refers to a compound with the following structural formula:

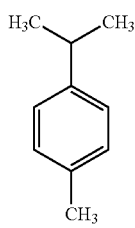

Within the context of this disclosure, the term "cymene" comprises any derivative and/or salt thereof, including any isomeric, structural and/or enantiomeric, variations thereof. In one embodiment, the compositions and methods disclosed herein comprise administering a formulation of cymene and a first psilocybin derivative. In one embodiment, the compositions and methods disclosed herein comprise administering a formulation of purified cymene and a first psilocybin derivative. In one embodiment, the compositions and methods disclosed herein comprise administering a formulation of cymene and a first purified psilocybin derivative. In one embodiment, the compositions and methods disclosed herein comprise administering a formulation of purified cymene and a first purified psilocybin derivative.

As used herein, the term "elemene" refers to a compound with the following structural formula:

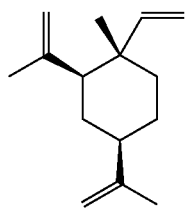

Within the context of this disclosure, the term "elemene" comprises any derivative and/or salt thereof, including any isomeric, structural and/or enantiomeric, variations thereof. In one embodiment, the compositions and methods disclosed herein comprise administering a formulation of elemene and a first psilocybin derivative. In one embodiment, the compositions and methods disclosed herein comprise administering a formulation of purified elemene and a first psilocybin derivative. In one embodiment, the compositions and methods disclosed herein comprise administering a formulation of elemene and a first purified psilocybin derivative. In one embodiment, the compositions and methods disclosed herein comprise administering a formulation of purified elemene and a first purified psilocybin derivative.

As used herein, the term "eucalyptol" refers to a compound with the following structural formula:

Within the context of this disclosure, the term "eucalyptol" comprises any derivative and/or salt thereof, including any isomeric, structural and/or enantiomeric, variations thereof. In one embodiment, the compositions and methods disclosed herein comprise administering a formulation of eucalyptol and a first psilocybin derivative. In one embodiment, the compositions and methods disclosed herein comprise administering a formulation of purified eucalyptol and a first psilocybin derivative. In one embodiment, the compositions and methods disclosed herein comprise administering a formulation of eucalyptol and a first purified psilocybin derivative. In one embodiment, the compositions and methods disclosed herein comprise administering a formulation of purified eucalyptol and a first purified psilocybin derivative.

As used herein, the term "eudesmol" refers to a compound with either of the following structural formulas:

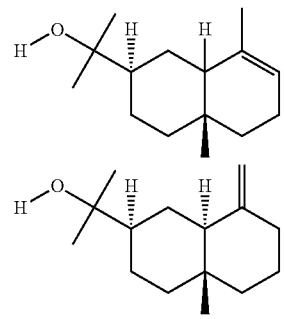

Within the context of this disclosure, the term "eudesmol" comprises any derivative and/or salt thereof, including any isomeric, structural and/or enantiomeric, variations thereof. In one embodiment, the compositions and methods disclosed herein comprise administering a formulation of eudesmol and a first psilocybin derivative. In one embodiment, the compositions and methods disclosed herein comprise administering a formulation of purified eudesmol and a first psilocybin derivative. In one embodiment, the compositions and methods disclosed herein comprise administering a formulation of eudesmol and a first purified psilocybin derivative. In one embodiment, the compositions and methods disclosed herein comprise administering a formulation of purified eudesmol and a first purified psilocybin derivative.

As used herein, the term "farnesene" refers to a compound with the following structural formula:

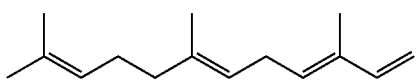

Within the context of this disclosure, the term "farnesene" comprises any derivative and/or salt thereof, including any isomeric, structural and/or enantiomeric, variations thereof. In one embodiment, the compositions and methods disclosed herein comprise administering a formulation of farnesene and a first psilocybin derivative. In one embodiment, the compositions and methods disclosed herein comprise administering a formulation of purified farnesene and a first psilocybin derivative. In one embodiment, the compositions and methods disclosed herein comprise administering a formulation of farnesene and a first purified psilocybin derivative. In one embodiment, the compositions and methods disclosed herein comprise administering a formulation of purified farnesene and a first purified psilocybin derivative.

As used herein, the term "fenchol" refers to a compound with the following structural formula:

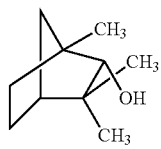

Within the context of this disclosure, the term "fenchol" comprises any derivative and/or salt thereof, including any isomeric, structural and/or enantiomeric, variations thereof. In one embodiment, the compositions and methods disclosed herein comprise administering a formulation of fenchol and a first psilocybin derivative. In one embodiment, the compositions and methods disclosed herein comprise administering a formulation of purified fenchol and a first psilocybin derivative. In one embodiment, the compositions and methods disclosed herein comprise administering a formulation of fenchol and a first purified psilocybin derivative. In one embodiment, the compositions and methods disclosed herein comprise administering a formulation of purified fenchol and a first purified psilocybin derivative.

As used herein, the term "geraniol" refers to a compound with the following structural formula:

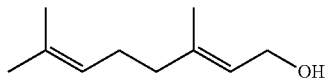

Within the context of this disclosure, the term "geraniol" comprises any derivative and/or salt thereof, including any isomeric, structural and/or enantiomeric, variations thereof. In one embodiment, the compositions and methods disclosed herein comprise administering a formulation of geraniol and a first psilocybin derivative. In one embodiment, the compositions and methods disclosed herein comprise administering a formulation of purified geraniol and a first psilocybin derivative. In one embodiment, the compositions and methods disclosed herein comprise administering a formulation of geraniol and a first purified psilocybin derivative. In one embodiment, the compositions and methods disclosed herein comprise administering a formulation of purified geraniol and a first purified psilocybin derivative.

As used herein, the term "guaiacol" refers to a compound with the following structural formula:

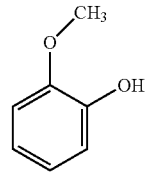

Within the context of this disclosure, the term "guaiacol" comprises any derivative and/or salt thereof, including any isomeric, structural and/or enantiomeric, variations thereof. In one embodiment, the compositions and methods disclosed herein comprise administering a formulation of guaiacol and a first psilocybin derivative. In one embodiment, the compositions and methods disclosed herein comprise administering a formulation of purified guaiacol and a first psilocybin derivative. In one embodiment, the compositions and methods disclosed herein comprise administering a formulation of guaiacol and a first purified psilocybin derivative. In one embodiment, the compositions and methods disclosed herein comprise administering a formulation of purified guaiacol and a first purified psilocybin derivative.

As used herein, the term "humulene" refers to a compound with the following structural formula:

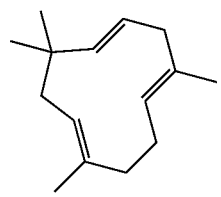

Within the context of this disclosure, the term "humulene" comprises any derivative and/or salt thereof, including any isomeric, structural and/or enantiomeric, variations thereof. In one embodiment, the compositions and methods disclosed herein comprise administering a formulation of humulene and a first psilocybin derivative. In one embodiment, the compositions and methods disclosed herein comprise administering a formulation of purified humulene and a first psilocybin derivative. In one embodiment, the compositions and methods disclosed herein comprise administering a formulation of humulene and a first purified psilocybin derivative. In one embodiment, the compositions and methods disclosed herein comprise administering a formulation of purified humulene and a first purified psilocybin derivative.

As used herein, the term "isoborneol" refers to a compound with the following structural formula:

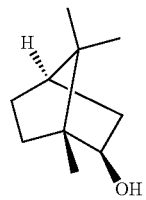

Within the context of this disclosure, the term "isoborneol" comprises any derivative and/or salt thereof, including any isomeric, structural and/or enantiomeric, variations thereof. In one embodiment, the compositions and methods disclosed herein comprise administering a formulation of isoborneol and a first psilocybin derivative. In one embodiment, the compositions and methods disclosed herein comprise administering a formulation of purified isoborneol and a first psilocybin derivative. In one embodiment, the compositions and methods disclosed herein comprise administering a formulation of isoborneol and a first purified psilocybin derivative. In one embodiment, the compositions and methods disclosed herein comprise administering a formulation of purified isoborneol and a first purified psilocybin derivative.

As used herein, the term "limonene" refers to a compound with the following structural formula:

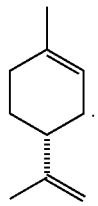

Within the context of this disclosure, the term "limonene" comprises any derivative and/or salt thereof, including any isomeric, structural and/or enantiomeric, variations thereof. In one embodiment, the compositions and methods disclosed herein comprise administering a formulation of limonene and a first psilocybin derivative. In one embodiment, the compositions and methods disclosed herein comprise administering a formulation of purified limonene and a first psilocybin derivative. In one embodiment, the compositions and methods disclosed herein comprise administering a formulation of limonene and a first purified psilocybin derivative. In one embodiment, the compositions and methods disclosed herein comprise administering a formulation of purified limonene and a first purified psilocybin derivative.

As used herein, the term "linalool" refers to a compound with the following structural formula:

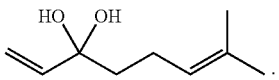

Within the context of this disclosure, the term "linalool" comprises any derivative and/or salt thereof, including any isomeric, structural and/or enantiomeric, variations thereof. In one embodiment, the compositions and methods disclosed herein comprise administering a formulation of linalool and a first psilocybin derivative. In one embodiment, the compositions and methods disclosed herein comprise administering a formulation of purified linalool and a first psilocybin derivative. In one embodiment, the compositions and methods disclosed herein comprise administering a formulation of linalool and a first purified psilocybin derivative. In one embodiment, the compositions and methods disclosed herein comprise administering a formulation of purified linalool and a first purified psilocybin derivative.

As used herein, the term "menthol" refers to a compound with the following structural formula:

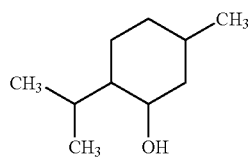

Within the context of this disclosure, the term "menthol" comprises any derivative and/or salt thereof, including any isomeric, structural and/or enantiomeric, variations thereof. In one embodiment, the compositions and methods disclosed herein comprise administering a formulation of menthol and a first psilocybin derivative. In one embodiment, the compositions and methods disclosed herein comprise administering a formulation of purified menthol and a first psilocybin derivative. In one embodiment, the compositions and methods disclosed herein comprise administering a formulation of menthol and a first purified psilocybin derivative. In one embodiment, the compositions and methods disclosed herein comprise administering a formulation of purified menthol and a first purified psilocybin derivative.

As used herein, the term "beta-myrcene" refers to a compound with the following structural formula:

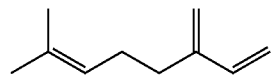

Within the context of this disclosure, the term "beta-myrcene" comprises any derivative and/or salt thereof, including any isomeric, structural and/or enantiomeric, variations thereof. In one embodiment, the compositions and methods disclosed herein comprise administering a formulation of beta-myrcene and a first psilocybin derivative. In one embodiment, the compositions and methods disclosed herein comprise administering a formulation of purified beta-myrcene and a first psilocybin derivative. In one embodiment, the compositions and methods disclosed herein comprise administering a formulation of beta-myrcene and a first purified psilocybin derivative. In one embodiment, the compositions and methods disclosed herein comprise administering a formulation of purified beta-myrcene and a first purified psilocybin derivative.

As used herein, the term "nerolidol" refers to a compound with the following structural formula:

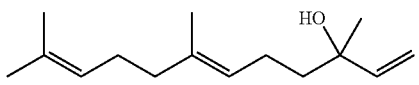 [SMILES: C=CC(C)(O)CC/C=C(\C)CCC=C(C)C]

Within the context of this disclosure, the term "nerolidol" comprises any derivative and/or salt thereof, including any isomeric, structural and/or enantiomeric, variations thereof. In one embodiment, the compositions and methods disclosed herein comprise administering a formulation of nerolidol and a first psilocybin derivative. In one embodiment, the compositions and methods disclosed herein comprise administering a formulation of purified nerolidol and a first psilocybin derivative. In one embodiment, the compositions and methods disclosed herein comprise administering a formulation of nerolidol and a first purified psilocybin derivative. In one embodiment, the compositions and methods disclosed herein comprise administering a formulation of purified nerolidol and a first purified psilocybin derivative.

As used herein, the term "ocimene" refers to a compound with the following structural formula:

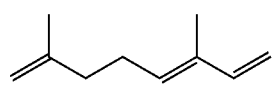

Within the context of this disclosure, the term "ocimene" comprises any derivative and/or salt thereof, including any isomeric, structural and/or enantiomeric, variations thereof.

In one embodiment, the compositions and methods disclosed herein comprise administering a formulation of ocimene and a first psilocybin derivative. In one embodiment, the compositions and methods disclosed herein comprise administering a formulation of purified ocimene and a first psilocybin derivative. In one embodiment, the compositions and methods disclosed herein comprise administering a formulation of ocimene and a first purified psilocybin derivative. In one embodiment, the compositions and methods disclosed herein comprise administering a formulation of purified ocimene and a first purified psilocybin derivative.

As used herein, the term "phellandrene" refers to a compound with the following structural formula:

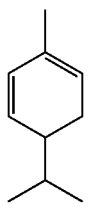

Within the context of this disclosure, the term "phellandrene" comprises any derivative and/or salt thereof, including any isomeric, structural and/or enantiomeric, variations thereof. In one embodiment, the compositions and methods disclosed herein comprise administering a formulation of phellandrene and a first psilocybin derivative. In one embodiment, the compositions and methods disclosed herein comprise administering a formulation of purified phellandrene and a first psilocybin derivative. In one embodiment, the compositions and methods disclosed herein comprise administering a formulation of phellandrene and a first purified psilocybin derivative. In one embodiment, the compositions and methods disclosed herein comprise administering a formulation of purified phellandrene and a first purified psilocybin derivative.

As used herein, the term "phytol" refers to a compound with the following structural formula:

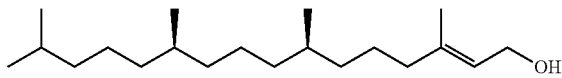 [SMILES: C/C(=C\CO)CCC[C@H](C)CCC[C@H](C)CCCC(C)C]

Within the context of this disclosure, the term "phytol" comprises any derivative and/or salt thereof, including any isomeric, structural and/or enantiomeric, variations thereof. In one embodiment, the compositions and methods disclosed herein comprise administering a formulation of phytol and a first psilocybin derivative. In one embodiment, the compositions and methods disclosed herein comprise administering a formulation of purified phytol and a first psilocybin derivative. In one embodiment, the compositions and methods disclosed herein comprise administering a formulation of phytol and a first purified psilocybin derivative. In one embodiment, the compositions and methods disclosed herein comprise administering a formulation of purified phytol and a first purified psilocybin derivative.

As used herein, the term "pinene" refers to a compound with the following structural formula:

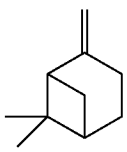

Within the context of this disclosure, the term "pinene" comprises any derivative and/or salt thereof, including any isomeric, structural and/or enantiomeric, variations thereof. In one embodiment, the compositions and methods disclosed herein comprise administering a formulation of pinene and a first psilocybin derivative. In one embodiment, the compositions and methods disclosed herein comprise administering a formulation of purified pinene and a first psilocybin derivative. In one embodiment, the compositions and methods disclosed herein comprise administering a formulation of pinene and a first purified psilocybin derivative. In one embodiment, the compositions and methods disclosed herein comprise administering a formulation of purified pinene and a first purified psilocybin derivative.

As used herein, the term "pulegone" refers to a compound with the following structural formula:

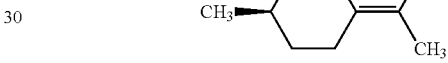

Within the context of this disclosure, the term "pulegone" comprises any derivative and/or salt thereof, including any isomeric, structural and/or enantiomeric, variations thereof. In one embodiment, the compositions and methods disclosed herein comprise administering a formulation of pulegone and a first psilocybin derivative. In one embodiment, the compositions and methods disclosed herein comprise administering a formulation of purified pulegone and a first psilocybin derivative. In one embodiment, the compositions and methods disclosed herein comprise administering a formulation of pulegone and a first purified psilocybin derivative. In one embodiment, the compositions and methods disclosed herein comprise administering a formulation of purified pulegone and a first purified psilocybin derivative.

As used herein, the term "sabinene" refers to a compound with the following structural formula:

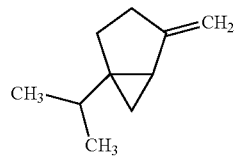

Within the context of this disclosure, the term "sabinene" comprises any derivative and/or salt thereof, including any isomeric, structural and/or enantiomeric, variations thereof. In one embodiment, the compositions and methods disclosed herein comprise administering a formulation of sabinene and a first psilocybin derivative. In one embodiment, the compositions and methods disclosed herein comprise administering a formulation of purified sabinene and a first psilocybin derivative. In one embodiment, the compositions and methods disclosed herein comprise administering a formulation of sabinene and a first purified psilocybin derivative. In one embodiment, the compositions and methods disclosed herein comprise administering a formulation of purified sabinene and a first purified psilocybin derivative.

As used herein, the term "terpineol" refers to a compound with the following structural formula:

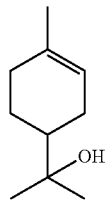

Within the context of this disclosure, the term "terpineol" comprises any derivative and/or salt thereof, including any isomeric, structural and/or enantiomeric, variations thereof. In one embodiment, the compositions and methods disclosed herein comprise administering a formulation of terpineol and a first psilocybin derivative. In one embodiment, the compositions and methods disclosed herein comprise administering a formulation of purified terpineol and a first psilocybin derivative. In one embodiment, the compositions and methods disclosed herein comprise administering a formulation of terpineol and a first purified psilocybin derivative. In one embodiment, the compositions and methods disclosed herein comprise administering a formulation of purified terpineol and a first purified psilocybin derivative.

As used herein, the term "terpinolene" refers to a compound with the following structural formula:

Within the context of this disclosure, the term "terpinolene" comprises any derivative and/or salt thereof, including any isomeric, structural and/or enantiomeric, variations thereof. In one embodiment, the compositions and methods disclosed herein comprise administering a formulation of terpinolene and a first psilocybin derivative. In one embodiment, the compositions and methods disclosed herein comprise administering a formulation of purified terpinolene and a first psilocybin derivative. In one embodiment, the compositions and methods disclosed herein comprise administering a formulation of terpinolene and a first purified psilocybin derivative. In one embodiment, the compositions and methods disclosed herein comprise administering a formulation of purified terpinolene and a first purified psilocybin derivative.

As used herein, the term "valencene" refers to a compound with the following structural formula:

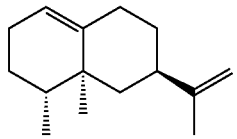

Within the context of this disclosure, the term "valencene" comprises any derivative and/or salt thereof, including any isomeric, structural and/or enantiomeric, variations thereof. In one embodiment, the compositions and methods disclosed herein comprise administering a formulation of valencene and a first psilocybin derivative. In one embodiment, the compositions and methods disclosed herein comprise administering a formulation of purified valencene and a first psilocybin derivative. In one embodiment, the compositions and methods disclosed herein comprise administering a formulation of valencene and a first purified psilocybin derivative. In one embodiment, the compositions and methods disclosed herein comprise administering a formulation of purified valencene and a first purified psilocybin derivative.

In one embodiment, the compositions disclosed herein comprise a particular ratio (e.g., a molar ratio) between about 100:1 to about 1:100 of the first purified psilocybin derivative and the first purified terpene.

In one embodiment, the compositions disclosed herein comprise a particular ratio (e.g., a molar ratio) between about 75:1 to about 1:75 of the first purified psilocybin derivative and the first purified terpene.

In one embodiment, the compositions disclosed herein comprise a particular ratio (e.g., a molar ratio) between about 50:1 to about 1:50 of the first purified psilocybin derivative and the first purified terpene.

In one embodiment, the compositions disclosed herein comprise a particular ratio (e.g., a molar ratio) between about 25:1 to about 1:25 of the first purified psilocybin derivative and the first purified terpene.

In one embodiment, the compositions disclosed herein comprise a particular ratio (e.g., a molar ratio) between about 10:1 to about 1:10 of the first purified psilocybin derivative and the first purified terpene.

In one embodiment, the compositions disclosed herein comprise a particular ratio (e.g., a molar ratio) between about 5:1 to about 1:5 of the first purified psilocybin derivative and the first purified terpene.

In one embodiment, the compositions and methods disclosed herein comprise a first purified psilocybin derivative, a first purified cannabinoid, and a first purified terpene.

In one embodiment, the compositions disclosed herein comprise a particular ratio (e.g., a molar ratio) between about 100:1 to about 1:100 of the first purified psilocybin derivative and the first purified cannabinoid and a particular ratio (e.g., a molar ratio) between about 100:1 to about 1:100 of the first purified psilocybin derivative and the first purified terpene.

In one embodiment, the compositions disclosed herein comprise a particular ratio (e.g., a molar ratio) between about 75:1 to about 1:75 of the first purified psilocybin derivative and the first purified cannabinoid and a particular ratio (e.g., a molar ratio) between about 75:1 to about 1:75 of the first purified psilocybin derivative and the first purified terpene.

In one embodiment, the compositions disclosed herein comprise a particular ratio (e.g., a molar ratio) between about 50:1 to about 1:50 of the first purified psilocybin derivative and the first purified cannabinoid and a particular ratio (e.g., a molar ratio) between about 50:1 to about 1:50 of the first purified psilocybin derivative and the first purified terpene.

In one embodiment, the compositions disclosed herein comprise a particular ratio (e.g., a molar ratio) between about 25:1 to about 1:25 of the first purified psilocybin derivative and the first purified cannabinoid and a particular ratio (e.g., a molar ratio) between about 25:1 to about 1:25 of the first purified psilocybin derivative and the first purified terpene.

In one embodiment, the compositions disclosed herein comprise a particular ratio (e.g., a molar ratio) between about 10:1 to about 1:10 of the first purified psilocybin derivative and the first purified cannabinoid and a particular ratio (e.g., a molar ratio) between about 10:1 to about 1:10 of the first purified psilocybin derivative and the first purified terpene.

In one embodiment, the compositions disclosed herein comprise a particular ratio (e.g., a molar ratio) between about 5:1 to about 1:5 of the first purified psilocybin derivative and the first purified cannabinoid and a particular ratio (e.g., a molar ratio) between about 5:1 to about 1:5 of the first purified psilocybin derivative and the first purified terpene.

In one embodiment, a first purified terpene modulates the activity of a neurotransmitter activity modulator, e.g., a serotonergic drug, an adrenergic drug, a dopaminergic drug, a psilocybin derivative, etc.

As used herein, the term "serotonergic drug" refers to a compound that binds to, blocks, or otherwise influences (e.g., via an allosteric reaction) activity at a serotonin receptor. In one embodiment, a serotonergic drug binds to a serotonin receptor. In one embodiment, a serotonergic drug indirectly affects a serotonin receptor, e.g., via interactions affecting the reactivity of other molecules at the serotonin receptor. In one embodiment, a serotonergic drug is an agonist, e.g., a compound activating a serotonin receptor. In one embodiment, a serotonergic drug is an antagonist, e.g., a compound binding but not activating a serotonin receptor, e.g., blocking a receptor. In one embodiment, a serotonergic drug is an effector molecule, e.g., a compound binding to an enzyme for allosteric regulation. In one embodiment, a serotonergic drug acts (either directly or indirectly) at more than one type of receptor (e.g., 5HT, dopamine, adrenergic, acetylcholine, etc.).

In one embodiment, a serotonergic drug is an antidepressant.

In one embodiment, a serotonergic drug is an anxiolytic.

In one embodiment, a serotonergic drug is a selective serotonin reuptake inhibitor.

In one embodiment, a serotonergic drug is a selective serotonin norepinephrine reuptake inhibitor.

Some exemplary serotonergic drugs include the following molecules: 6-Allyl-N,N-diethyl-NL, N,N-Dibutyl-T, N,N-Diethyl-T, N,N-Diisopropyl-T, 5-Methyoxy-alpha-methyl-T, N,N-Dimethyl-T, 2,alpha-Dimethyl-T, alpha,N-Dimethyl-T, N,N-Dipropyl-T, N-Ethyl-N-isopropyl-T, alpha-Ethyl-T, 6,N,N-Triethyl-NL, 3,4-Dihydro-7-methoxy-1-methyl-C, 7-Methyoxy-1-methyl-C, N,N-Dibutyl-4-hydroxy-T, N,N-Diethyl-4-hydroxy-T, N,N-Diisopropyl-4-hydroxy-T, N,N-Dimethyl-4-hydroxy-T, N,N-Dimethyl-5-hydroxy-T, N,N-Dipropyl-4-hydroxy-T, N-Ethyl-4-hydroxy-N-methyl-T, 4-Hydroxy-N-isopropyl-N-methyl-T, 4-Hydroxy-N-methyl-N-propyl-T, 4-Hydroxy-N,N-tetramethylene-T Ibogaine, N,N-Diethyl-L, N-Butyl-N-methyl-T, N,N-Diisopropyl-4,5-methylenedioxy-T, N,N-Diisopropyl-5,6-methylenedioxy-T, N,N-Dimethyl-4,5-methylenedioxy-T, N,N-Dimethyl-5,6-methylenedioxy-T, N-Isopropyl-N-methyl-5,6-methylenedioxy-T, N,N-Diethyl-2-methyl-T, 2,N,N-Trimethyl-T, N-Acetyl-5-methoxy-T, N,N-Diethyl-5-methoxy-T, N,N-Diisopropyl-5-methoxy-T, 5-Methoxy-N,N-dimethyl-T, N-Isopropyl-4-methoxy-N-methyl-T, N-Isopropyl-5-methoxy-N-methyl-T, 5,6-Dimethoxy-N-isopropyl-N-methyl-T, 5-Methoxy-N-methyl-T, 5-Methoxy-N,N-tetramethylene-T, 6-Methoxy-1-methyl-1,2,3,4-tetrahydro-C, 5-Methoxy-2,N,N-trimethyl-T, N,N-Dimethyl-5-methylthio-T, N-Isopropyl-N-methyl-T, alpha-Methyl-T, N-Ethyl-T, N-Methyl-T, 6-Propyl-NL, N,N-Tetramethylene-T, Tryptamine, and 7-Methoxy-1-methyl-1,2,3,4-tetrahydro-C, alpha,N-Dimethyl-5-methoxy-T. For additional information regarding these compounds See Shulgin, A. T., & Shulgin, A. (2016). *Tihkal: The Continuation*. Berkeley, CA: Transform Press.

In one embodiment, a serotonergic drug is chosen from alprazolam, amphetamine, aripiprazole, azapirone, a barbiturate, bromazepam, bupropion, buspirone, a cannabinoid, chlordiazepoxide, citalopram, clonazepam, clorazepate, dextromethorphan, diazepam, duloxetine, escitalopram, fluoxetine, flurazepam, fluvoxamine, lorazepam, lysergic acid diethylamide, lysergamide, 3,4-methylenedioxymethamphetamine, milnacipran, mirtazapine, naratriptan, paroxetine, pethidine, phenethylamine, psicaine, oxazepam, reboxetine, serenic, serotonin, sertraline, temazepam, tramadol, triazolam, a tryptamine, venlafaxine, vortioxetine, and/or derivatives thereof.

As used herein, the term "serotonin" refers to a neurotransmitter compound with the following structural formula:

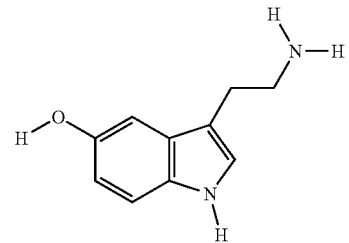 [SMILES: NCCc1c[nH]c2ccc(O)cc12]

In one embodiment, serotonin acts at a serotonin receptor, e.g., by acting as a ligand at a 5-HT receptor. In one embodiment, serotonin is produced by an organism for use as a neurotransmitter within that organism. In one embodiment, the compositions disclosed herein increase the activity at a serotonin receptor. In one embodiment, the compositions disclosed herein decrease the activity at a serotonin receptor.

As used herein, the term "serotonin receptor" refers to a collection of proteins outside a cell capable of receiving signals and activating internal signal transduction pathways causing a cellular response. In one embodiment, a serotonin receptor is found on a cell within the central nervous system of an organism. In one embodiment, a serotonin receptor is found on a cell within the peripheral nervous system of an organism. In one embodiment, serotonin is the natural ligand for a serotonin receptor. In one embodiment, a serotonin receptor modulates the release of a neurotransmitter, e.g., glutamate, gamma-Aminobutyric acid, dopamine, epinephrine (a.k.a. norepinephrine), acetylcholine, etc. In one embodiment, a serotonin receptor modulates the release of a hormone, e.g., oxytocin, prolactin, vasopressin, cortisol, corticotropin, substance P, etc.

Examples of serotonin receptors include, but are not limited to, $5\text{-}HT_{1A}$, $5\text{-}HT_{1B}$, $5\text{-}HT_{1D}$, $5\text{-}HT_{1E}$, $5\text{-}HT_{1F}$, $5\text{-}HT_{2A}$, $5\text{-}HT_{2B}$, $5\text{-}HT_{2C}$, $5\text{-}HT_3$, $5\text{-}HT_4$, $5\text{-}HT_{5A}$, $5\text{-}HT_{5B}$, $5\text{-}HT_6$, and $5\text{-}HT_7$.

As used herein, the term "adrenergic drug" refers to a compound that binds, blocks, or otherwise influences (e.g., via an allosteric reaction) activity at an adrenergic receptor. In one embodiment, an adrenergic drug binds to an adrenergic receptor. In one embodiment, an adrenergic drug indirectly affects an adrenergic receptor, e.g., via interactions affecting the reactivity of other molecules at the adrenergic receptor. In one embodiment, an adrenergic drug is an agonist, e.g., a compound activating an adrenergic receptor. In one embodiment, an adrenergic drug is an antagonist, e.g., a compound binding but not activating an adrenergic receptor, e.g., blocking a receptor. In one embodiment, an adrenergic drug is an effector molecule, e.g., a compound binding to an enzyme for allosteric regulation. In one embodiment, an adrenergic drug acts (either directly or indirectly) at more than one type of receptor (e.g., 5HT, dopamine, adrenergic, acetylcholine, etc.).

In one embodiment, an adrenergic drug is an antidepressant.

In one embodiment, an adrenergic drug is a norepinephrine transporter inhibitor.

In one embodiment, an adrenergic drug is a vesicular monoamine transporter inhibitor.

In one embodiment, an adrenergic drug is chosen from adrenaline, agmatine, amoxapine, aptazapine, atomoxetine, bupropion, clonidine, doxepin, duloxetine, esmirtazpine, mianserin, mirabegron, mirtazapine, norepinephrine, phentolamine, phenylephrine, piperoxan, reserpine, ritodrine, setiptiline, tesofensine, timolol, trazodone, trimipramine, or xylazine.

As used herein, the term "adrenaline", also known as "epinephrine", refers to a neurotransmitter compound with the following structural formula:

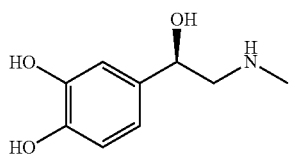

In one embodiment, adrenaline acts at an adrenergic receptor, e.g., by acting as a ligand at an adrenergic receptor. In one embodiment, adrenaline is produced by an organism for use as a neurotransmitter within that organism. In one embodiment, the compositions disclosed herein increase the activity at an adrenergic receptor. In one embodiment, the compositions disclosed herein decrease the activity at an adrenergic receptor.

As used herein, the term "adrenergic receptor" refers to a collection of proteins outside a cell capable of receiving signals and activating internal signal transduction pathways causing a cellular response. In one embodiment, an adrenergic receptor is found on a cell within the central nervous system of an organism. In one embodiment, an adrenergic receptor is found on a cell within the sympathetic nervous system of an organism.

Examples of adrenergic receptors include, but are not limited to, $\alpha_1 A$, $\alpha_1 B$, $\alpha_1 D$, $\alpha_2 A$, $\alpha_2 B$, $\alpha_2 C$, $\beta_1$, $\beta_2$, and $\beta_3$.

As used herein, the term "norepinephrine" refers to a neurotransmitter compound with the following structural formula:

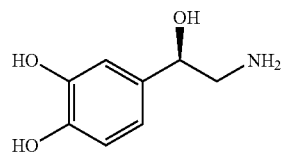 [SMILES: NC[C@H](O)c1ccc(O)c(O)c1]

In one embodiment, norepinephrine acts at an adrenergic receptor, e.g., by acting as a ligand at an adrenergic receptor. In one embodiment, norepinephrine is produced by an organism for use as a neurotransmitter within that organism. In one embodiment, the compositions disclosed herein increase the activity at an adrenergic receptor. In one embodiment, the compositions disclosed herein decrease the activity at an adrenergic receptor.

As used herein, the term "dopaminergic drug" refers to a compound that binds, blocks, or otherwise influences (e.g., via an allosteric reaction) activity at a dopamine receptor. In one embodiment, a dopaminergic drug binds to a dopamine receptor. In one embodiment, a dopaminergic drug indirectly affects a dopamine receptor, e.g., via interactions affecting the reactivity of other molecules at the dopamine receptor. In one embodiment, a dopaminergic drug is an agonist, e.g., a compound activating a dopamine receptor. In one embodiment, a dopaminergic drug is an antagonist, e.g., a compound binding but not activating a dopamine receptor, e.g., blocking a receptor. In one embodiment, a dopaminergic drug is an effector molecule, e.g., a compound binding to an enzyme for allosteric regulation. In one embodiment, a dopaminergic drug acts (either directly or indirectly) at more than one type of receptor (e.g., 5HT, dopamine, adrenergic, acetylcholine, etc.).

In one embodiment, a dopaminergic drug is a dopamine transporter inhibitor.

In one embodiment, a dopaminergic drug is a vesicular monoamine transporter inhibitor.

In one embodiment, a dopaminergic drug is chosen from amineptine, apomorphine, benzylpiperazine, bromocriptine, cabergoline, chlorpromazine, clozapine, dihydrexidine, domperidone, dopamine, fluphenazine, haloperidol, ketamine, loxapine, methamphetamine, olanzapine, pemoline, perphenazine, pergolide, phencyclidine, phenethylamine, phenmetrazine, pimozide, piribedil, a psychostimulant, reserpine, risperidone, ropinirole, tetrabenazine, or thioridazine.

As used herein, the term "dopamine" refers to a neurotransmitter compound with the following structural formula:

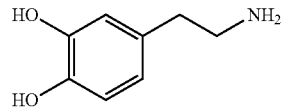 [SMILES: NCCc1ccc(O)c(O)c1]

In one embodiment, dopamine acts at a dopamine receptor, e.g., by acting as a ligand at a dopamine receptor. In one embodiment, dopamine is produced by an organism for use as a neurotransmitter within that organism. In one embodiment, the compositions disclosed herein increase the activity at a dopamine receptor. In one embodiment, the compositions disclosed herein decrease the activity at a dopamine receptor.

As used herein, the term "dopamine receptor" refers to a collection of proteins outside a cell capable of receiving signals and activating internal signal transduction pathways causing a cellular response. In one embodiment, a dopamine receptor is found on a cell within the central nervous system of an organism.

Examples of dopamine receptors include, but are not limited to, $D_1$, $D_2$, $D_{25h}$, $D_{2Lh}$, $D_3$, $D_4$, and $D_5$.

In one embodiment, a first purified terpene modulates the activity of a neurotransmitter at its native receptor, e.g., serotonin at a serotonin receptor, dopamine at a dopaminergic drug, norephedrine at an adrenergic receptor, etc.

In one embodiment, a first purified terpene is active at one or more receptors, e.g., a serotonin receptor, an adrenergic receptor, a dopamine receptor, a GABAergic receptor, a glutaminergic receptor, a histaminergic receptor, a cholinergic receptor, an opioid receptor, or a glycinergic receptor.

In one embodiment, the methods and compositions disclosed herein comprise an excipient.

As used herein, the term "excipient" refers to a compound useful for increasing the bioavailability of an active ingredient or ingredients. In one embodiment, an excipient allows for quicker absorption of an active ingredient into a human body. In one embodiment, an excipient binds to a compound thereby providing faster permeability across membranes, barriers, walls, etc. In one embodiment, the methods disclosed herein comprise administering two or more excipients, e.g., a pH buffer, an antioxidant, etc. In one embodiment, an excipient also functions as a stabilizer. In one embodiment, an excipient binds two or more compounds forming a homogeneous mixture within a solution, e.g., a purified water insoluble compound (e.g., a cannabinoid or terpene) and a purified psilocybin derivative (water soluble) forming a homogeneous mixture in water.

Examples of excipients are, but are not limited to, sodium lauryl sulfate, sucrose, alcohol, gelatin, polyvinylpyrrolidone, methionine, Vitamin E TPGS, dimethyl sulfoxide, tartrazine, polyethylene glycol, magnesium stearate, stearic acid, fumed silica, talc, magnesium carbonate, or benzalkonium chloride.

In one embodiment, the compositions disclosed herein comprise a monoamine oxidase inhibitor.

As used herein, the term "monoamine oxidase inhibitor" refers to a molecule binding to a monoamine oxidase enzyme thereby reducing the activity of the monoamine oxidase enzyme. Within the context of this disclosure, examples of monoamine oxidase inhibitors include aurorix, deprenyl, eldepryl, emsam, humoryl, hydracarbazine, isocarboxazid, linezolid, manerix, nydrazid, phenelzine, pirazidol, procarbazine, rasagiline, and tranylcypromine. In one embodiment, monoamine oxidase catalyzes the oxidation of a monoamine, e.g., serotonin, dopamine, norepinephrine, amphetamine, adrenaline, etc.

In one embodiment, the methods and compositions disclosed herein comprise a stabilizer.

As used herein, the term "stabilizer" refers to a compound useful for preventing the degradation of an active ingredient, e.g., a psilocybin derivative, a cannabinoid, a terpene, etc. In one embodiment, a stabilizer prevents a first psilocybin derivative from degrading. In one embodiment, a stabilizer prevents a first psilocybin derivative from reacting with other compounds in the composition, e.g., a cannabinoid, a terpene, a base, an acid, etc. In one embodiment, a stabilizer prevents a first psilocybin derivative from reacting with the ambient atmosphere, e.g., heat, light, water, and/or oxygen. In one embodiment, a stabilizer comprises an antioxidant. In one embodiment, a stabilizer comprises a pH buffer.

In one embodiment, the methods and compositions disclosed herein comprise an antioxidant.

As used herein, the term "antioxidant" refers to a compound and/or a composition useful for preventing oxidation. In one embodiment, an antioxidant protects an active ingredient from "free radicals". Within the context of disclosure, a "free radical" is an atom, molecule, or an ion with an unpaired valence electron. In one embodiment, an antioxidant is an electron donor.

In one embodiment, an antioxidant is chosen from ascorbic acid, lycopene, tocopherol, melatonin, retinol, astaxanthin, lutein, apigenin, carnosine, selenium, zinc, cucurmin, and/or a salt or derivative thereof.

In one embodiment, an antioxidant is ascorbic acid and/or its salts or derivatives. Within the context of this disclosure, the term "ascorbic acid" comprises Vitamin C and/or a salt or derivative thereof.

In one embodiment, an antioxidant prevents the oxidation of a composition comprising one or more compounds disclosed herein, e.g., psilocybin derivatives, cannabinoids, terpenes, and/or mixtures thereof. For example, preventing the oxidation of a phenolic group attached to a psilocybin derivative.

As used herein, the term "oxidation" refers to the formal loss of electrons and/or the increase of the formal oxidation state and/or the addition of an oxygen atom or atoms. "Reduction" refers to the formal gain of electrons and/or the decrease of the formal oxidation state. Zumdahl, Steven S., et al. *Chemistry, 7th*. Cengage Learning, 2018.

In one embodiment, an antioxidant prevents the oxidation of a composition comprising one or more compounds disclosed herein, e.g., psilocybin derivatives or mixtures thereof.

In one embodiment, the methods and compositions disclosed herein comprise a pH buffer.

As used herein, the term "pH buffer" refers to a compound or a composition useful for maintaining the pH of a composition. In one embodiment, a pH buffer comprises a weak acid and a corresponding conjugate base. In one embodiment, a pH buffer comprises a weak base and a corresponding conjugate acid. In one embodiment, a pH buffer does not change the pH of a composition with the addition of a strong acid and/or base.

In one embodiment, a pH buffer maintains the pH of a composition around 7.

In one embodiment, a pH buffer maintains the pH of a composition below 7.

In one embodiment, a pH buffer maintains the pH of a composition above 7.

In one embodiment, a pH buffer maintains the pH of a composition between 2-6.

In one embodiment, a pH buffer maintains the pH of a composition between 5-7.

In one embodiment, a pH buffer maintains the pH of a composition between 6-8.

In one embodiment, a pH buffer maintains the pH of a composition between 7-10.

In one embodiment, a pH buffer comprises citric acid, acetic acid, monosodium phosphate, N-Cyclohexyl-2-aminoethanesulfonic acid, borate, hydrochloric acid, and/or sodium hydroxide.

In one embodiment, the methods disclosed herein comprise administering a formulation comprising an acid.

As used herein, the term "acid" refers to a molecule or ion capable of donating a proton, i.e., H+ and/or accepting electrons. In one embodiment, an "acid" refers to a Lewis acid. In one embodiment, an "acid" refers to a Bronsted acid. In one embodiment, an acid is determined by a compositions pH. In one embodiment, a pH below 7 indicates the presence of an acid.

In one embodiment, the compositions and methods disclosed herein comprise administering a formulation comprising a base.

As used herein, the term "base" refers to a molecule or ion capable of accepting a proton, i.e., a H+. In one embodiment, a "base" refers to a molecule capable of donating an electron pair, i.e., a Lewis base. In one embodiment, the presence of a base is determined by a compound's pH. In one embodiment, a pH above 7 indicates the presence of a base.

In one embodiment, the compositions and methods disclosed herein comprise administering a water-soluble composition.

As used herein, the term "water soluble" refers to a compound capable of dissolving in water at standard temperature and pressure. In one example, 1 g of a compound dissolves in 1 L of water. In one example, 2 g of a compound dissolves in 1 L of water. In one example, 5 g of a compound dissolves in 1 L of water. In one example, 10 g of a compound dissolves in 1 L of water. In one embodiment, a compound's solubility in water is an inherent property of a compound. In one embodiment, a compound's solubility in water is facilitated by another compound, e.g., an excipient.

In one embodiment, the compositions and methods disclosed herein comprise a solvent.

As used herein, the term "solvent" refers to a compound or composition that discloses another (a solute), thereby creating a solution. In one embodiment, the solvent is water. In one embodiment, the solvent is an oil. In one embodiment, the solvent is an alcohol.

In one embodiment, the compositions and methods disclosed herein comprise administering a first purified psilocybin derivative present as and/or within a homogenous mixture within a first dosage formulation.

In one embodiment, the compositions and methods disclosed herein comprise administering a first purified psilocybin derivative and a first purified cannabinoid present as and/or within a homogenous mixture within a first dosage formulation.

In one embodiment, the compositions and methods disclosed herein comprise administering a first purified psilocybin derivative and a first purified terpene present as and/or within a homogenous mixture within a first dosage formulation.

In one embodiment, the compositions and methods disclosed herein comprise administering a first purified psilocybin derivative, a first purified cannabinoid, and a first purified terpene present as and/or within a homogenous mixture within a first dosage formulation.

In one embodiment, the compositions and methods disclosed herein comprise administering a first purified psilocybin derivative, a first purified cannabinoid, a first purified terpene, and an excipient present as and/or within a homogenous mixture within a first dosage formulation.

As used herein, the term "homogeneous mixture" refers to a solid, liquid, or gaseous composition that has two or more compounds present within one state or thing, e.g., a clear, colorless solution. In one embodiment, the homogeneous mixtures disclosed herein have the same proportion, concentration, and/or ratio of its components across different samples. In one embodiment, the components in the homogeneous mixture are in the same state of matter. In one embodiment, a homogeneous mixture comprises one or more compounds within a solution, e.g., a first psilocybin derivative and a first cannabinoid within a clear solution. In one embodiment, the compositions disclosed herein are present as a homogenous mixture, e.g., a solution with no particulates, a solution with equal concentrations across samples, a powder of similar particle size, etc.

In one embodiment, a homogeneous mixture is a solution comprising a first purified psilocybin derivative.

In one embodiment, a homogeneous mixture is a solution comprising a first purified psilocybin derivative and a first purified cannabinoid.

In one embodiment, a homogeneous mixture is a solution comprising a first purified psilocybin derivative and a first purified terpene.

In one embodiment, a homogeneous mixture is a solution comprising a first purified psilocybin derivative, a first purified cannabinoid, and a first purified terpene.

In one embodiment, a homogeneous mixture has little or no deviation in a chemical composition between across different samples taken of the compositions disclosed herein.

As used herein, the phrase "little or no deviation" means that different samples from the same composition are internally consistent. For example, two different 1 g aliquots, taken from the same 100 g sample, would have "little or no deviation" when they share substantially the same chemical composition when characterized by chromatography and/or spectrometry. By contrast, naturally occurring fungal fruiting bodies (aka mushrooms) or plants often show considerable deviation in the chemical concentration of certain compounds.

For example, the concentration of psilocybin and/or psilocin varies greatly across species of naturally occurring fungal fruiting bodies, e.g., 0 to 15 mg of psilocybin and/or psilocin per gram of dry plant material. Stafford, Peter. *Psychedelics Encyclopedia: Third Expanded Edition*. Ronin Publishing, 1993. Likewise, extracts taken from these highly variable samples are similarly variable.

The concentration of psilocybin and/or psilocin varies greatly between species and even between specimens of a species collected and/or grown from the same culture. Bigwood J, Beug M W (1982). "*Variation of psilocybin and psilocin levels with repeated flushes (harvests) of mature sporocarps of Psilocybe cubensis (Earle) Singer*". Journal of Ethnopharmacology. 5 (3): 287-91.

Moreover, the concentrations of molecules within different samples may change at different rates because of degradation, such as oxidative degradation and/or enzymatic degradation.

As an advance beyond the state of the art, the methods disclosed herein comprise administering compositions showing little or no deviation between aliquots taken from a particular batch. In one embodiment, a sample composition weighing 100 grams, each 1 gram portion deviates in chemical concentration by less than about 10% as compared to the currently available technology. In another embodiment, a sample weighing 100 grams, each 1 gram portion deviates in chemical concentration by less than about 5% as compared to the currently available technology. In another embodiment, a sample weighing 100 grams, each 1 gram portion would deviates in chemical concentration of less than about 1% as compared to the currently available technology.

In one embodiment, the compositions and methods disclosed herein comprise a dephosphorylating agent.

As used herein, the term "dephosphorylating agent" refers to a compound or composition capable of facilitating the removal of a phosphate group from a molecule comprising a phosphate group. In one embodiment, a dephosphorylating agent is kept physically separate (e.g., a film, a coating, or other barrier preventing mixing) from an active ingredient, e.g., a purified psilocybin derivative within a composition. In one embodiment, a dephosphorylating agent removes a phosphate group from a psilocybin derivative, e.g., psilocybin.

In one embodiment, the methods disclosed herein comprise dephosphorylating a psilocybin derivative.

As used herein, the term "dephosphorylating" refers to removing a phosphate group from a molecule having a phosphate group. In one embodiment, dephosphorylating a first purified psilocybin derivative comprises cleaving chemical bonds via hydrolysis. In one embodiment, dephosphorylating a first purified psilocybin derivative changes (e.g., increase) activity at one or more neurotransmitter receptors. In one embodiment, dephosphorylating a first purified psilocybin derivative occurs within an organism. In one embodiment, dephosphorylating a first purified psilocybin derivative occurs before administering a composition.

Disclosed herein is a method of modulating activity at a neurotransmitter receptor, comprising:
administering a neurotransmitter activity modulator; and
administering a first dosage formulation comprising a first purified psilocybin derivative to the person in need of treatment, wherein the first dosage formulation modulates activity at a neurotransmitter receptor.

As used herein, the term "modulating activity of the neurotransmitter activity modulator" refers to changing, manipulating, and/or adjusting the ability of a compound or composition to affect a neurotransmitter receptor. In one embodiment, modulating activity of a neurotransmitter activity modulator comprises administering an agonist at a neurotransmitter receptor. In one embodiment, modulating activity of a neurotransmitter activity modulator comprises administering an antagonist at a neurotransmitter receptor.

As used herein, the term "administering" (e.g., administering a drug) refers to dosing, treating, giving, and/or providing. In one embodiment, administering a neurotransmitter activity modulator comprises providing a neurotransmitter activity modulator to an organism with a neurotransmitter receptor, e.g., a human being. In one embodiment, administering a neurotransmitter activity modulator comprises providing a neurotransmitter activity modulator along with a purified psilocybin derivative, e.g., a formulation having each of a neurotransmitter activity modulator and a purified psilocybin derivative in a single dosage. In one embodiment, administering a neurotransmitter activity modulator comprises applying a transdermal composition, e.g., applying a topical composition to the skin having each of a neurotransmitter activity modulator and a purified psilocybin derivative. In one embodiment, administering a neurotransmitter activity modulator comprises giving a transmucosal preparation, e.g., providing rapidly dissolving a tablet with an absorption enhancer having each of a neurotransmitter activity modulator and a purified psilocybin derivative.

In one embodiment, the methods disclosed herein comprise transmucosally administering a composition for crossing a blood-brain barrier.

As used herein, the term "transmucosally administering" refers to providing a compound by entering through, or across, a mucous membrane, e.g., an oral administration of a composition. In one embodiment, transmucosally administering refers to delivering a drug via the cavity between the cheek and gum, e.g., a liquid composition, a fast dissolving tablet, a patch, etc. In one embodiment, transmucosally administering refers to delivering a drug under the tongue, e.g., a liquid composition, a fast dissolving tablet, a patch, etc. In one embodiment, transmucosally administering refers to delivering a drug via the upper gastrointestinal system, e.g., a sublingual formulation or liquid preparation with a permeation enhancer, a tablet, a food product, etc.

In one embodiment, the methods disclosed herein comprise transdermally administering a composition.

As used herein, the term "transdermally administering" refers to providing a compound by entering the blood or body through the dermis, or skin, of an organism. In one embodiment, transdermally administering comprises applying a composition to the skin of an organism, e.g., applying a topical composition, applying a liquid composition, etc. In one embodiment, transdermally administering a composition comprises applying a patch embedded with the composition to the skin of an organism.

As used herein, the term "neurotransmitter activity modulator" refers to a compound or composition that reacts or influences activity at a neurotransmitter receptor, e.g., a serotonergic drug, an adrenergic receptor, a dopamine receptor, a GABAergic receptor, a glutaminergic receptor, a histaminergic receptor, a cholinergic receptor, an opioid receptor, or a glycinergic receptor, etc. In one embodiment, a neurotransmitter activity modulator binds on a neurotransmitter receptor. In one embodiment, a neurotransmitter activity modulator indirectly affects a neurotransmitter receptor, e.g., via interactions affecting the reactivity of other molecules at a neurotransmitter receptor. In one embodiment, a neurotransmitter activity modulator is an agonist. In one embodiment, a neurotransmitter activity modulator is an antagonist. In one embodiment, a neurotransmitter activity modulator acts (either directly or indirectly) at more than one type of neurotransmitter receptor.

In one embodiment, a neurotransmitter activity modulator is chosen from aripiprazole, buproprion, citalopram, clomipramine, dextroamphetamine, duloxetine, escitalopram, fluoxetine, fluvoxamine, milnacipran, mirtazapine, paroxetine, quetiapine, reboxetine, risperidone, sertraline, and venlafaxine.

As used herein, the term "first dosage formulation" refers to a compound or compounds selected for the purposes of causing a reaction, effect, and/or result, e.g., causing activity at a neurotransmitter receptor, reacting with other compounds, enhancing the effects of other active ingredients, inhibiting the biosynthesis of a compound, etc., within an organism. In one embodiment, a first dosage formulation comprises a first purified psilocybin derivative. In one embodiment, a first dosage formulation comprises a first purified cannabinoid. In one embodiment, a first dosage formulation comprises a first purified terpene. In one embodiment, a first dosage formulation comprises a first purified psilocybin derivative and a second purified psilocybin derivative. In one embodiment, a first dosage formulation comprises a first purified psilocybin derivative and a first purified cannabinoid. In one embodiment, a first dosage formulation comprises a first purified psilocybin derivative and a first purified terpene. In one embodiment, a first dosage formulation comprises a first purified psilocybin derivative, a first purified cannabinoid, and first purified terpene. In one embodiment, a first dosage formulation comprises a first purified psilocybin derivative, and a neurotransmitter activity modulator.

In one embodiment, a second dosage formulation comprises a first purified psilocybin derivative. In one embodiment, a second dosage formulation comprises a second purified psilocybin derivative. In one embodiment, a second dosage formulation comprises a first purified cannabinoid. In one embodiment, a second dosage formulation comprises a first purified terpene. In one embodiment, a second dosage formulation comprises a first purified psilocybin derivative and a first purified cannabinoid. In one embodiment, a second dosage formulation comprises a first purified psilocybin derivative and a first purified terpene. In one embodiment, a second dosage formulation comprises a first purified psilocybin derivative, a first purified cannabinoid, and a first purified terpene. In one embodiment, a second dosage formulation comprises a first purified psilocybin derivative, and a neurotransmitter activity modulator.

In one embodiment, the methods disclosed herein comprise administering a second dosage formulation. In one embodiment, the methods disclosed herein comprise administering a third dosage formulation. In one embodiment, the methods disclosed herein comprise administering a fourth dosage formulation. In one embodiment, the methods disclosed herein comprise administering more than four dosage formulations.

In one embodiment, the methods disclosed herein comprise administering one or more active ingredients, e.g., psilocybin derivatives, cannabinoids, terpenes, neurotransmitter activity modulators, etc., in a single dosage, e.g., a single tablet, a single composition, a single formulation, etc.

In one embodiment, the methods disclosed herein comprise administering one or more active ingredients, e.g., psilocybin derivatives, cannabinoids, terpenes, neurotransmitter activity modulators, etc., in more than two doses, e.g., two or more tablets, two or more compositions, two or more formulations, etc.

Disclosed herein is a method of treating a psychological problem, comprising:
  identifying a person in need of treatment; and
  administering a first purified psilocybin derivative to the person in need of treatment, wherein the first purified psilocybin derivative modulates activity at a neurotransmitter receptor.

As used herein, the term "identifying a person in need of treatment" refers to analyzing, diagnosing, and/or determining whether a person requires a composition modulating the activity at a neurotransmitter receptor. In one embodiment, identifying a person in need of treatment comprises diagnosing a person with a medical condition, e.g., a neurological disorder, a chemical imbalance, a hereditary condition, etc. In one embodiment, identifying a person in need of treatment comprises performing a psychiatric evaluation. In one embodiment, identifying a person in need of treatment comprises performing a blood test. In one embodiment, identifying a person in need of treatment comprises determining whether a person has a compulsive disorder. In one embodiment, identifying a person in need of treatment comprises self identifying as having a compulsive disorder.

As used herein, the term "psychological disorder" refers to a condition wherein a person exhibits a pattern of behavioral and/or psychological symptoms that impact multiple life areas and create distress for the person experiencing these symptoms. In one embodiment, a psychological disorder is caused by a genetic disorder. In one embodiment, a psychological disorder is caused by a biological condition, e.g., excess hormone production, a lack of activity at a neurotransmitter receptor, a lack of producing neurotransmitters, etc. In one embodiment, the neurotransmitter receptor is a serotonin receptor.

In one embodiment, the psychological problem is an anxiety disorder. In one embodiment, the psychological problem is a depressive disorder. In one embodiment, the psychological problem is a compulsive disorder.

As used herein, the term "anxiety disorder" refers to a state of apprehension, uncertainty, and/or fear resulting from the anticipation of an event and/or situation. An anxiety disorder can disrupt the physical and psychological functions of a person. These disruptions can cause a small hindrance to a debilitating handicap for a person's everyday life. An anxiety disorder can cause a physiological symptom, e.g., muscle tension, heart palpitations, sweating, dizziness, shortness of breath, etc. An anxiety disorder can also cause a psychological symptom, e.g., fear of dying, fear of embarrassment or humiliation, fear of an event occurring, etc.

In one embodiment, an anxiety disorder comprises acute stress disorder, anxiety due to a medical condition, generalized anxiety disorder, panic disorder, panic attack, a phobia, post traumatic stress disorder, separation anxiety disorder, social anxiety disorder, substance-induced anxiety disorder, or selective mutism.

As used herein, the term "acute stress disorder" refers to a condition developed after exposure to one or more traumatic events. Examples of traumatic events include, but are not limited to, exposure to war, rape or sexual violence, a physical attack, a mugging, childhood physical or sexual violence, kidnapping or being taken hostage, terrorist attacks, torture, nature disasters and/or severe accidents. In one embodiment, acute stress disorder occurs within a day of experiencing a traumatic event. In one embodiment, acute stress disorder occurs within three days of experiencing a traumatic event. In some instances, acute stress disorder occurs within a week of experiencing a traumatic event. In some instances, acute stress disorder occurs within a month of experiencing a traumatic event.

As used herein, the term "anxiety due to another medical condition" refers to a condition wherein anxiety symptoms are developed because of a physiological and psychological consequence of a non-related disease, injury, and/or illness, e.g., an endocrine disease, a cardiovascular disorder, respiratory illness, a metabolic disturbance, a neurological illness, etc.

As used herein, the term "generalized anxiety disorder" refers to a condition of persistent and excessive anxiety and worry about various domains, e.g., work, school, social settings, etc., that an individual finds difficult to control. In addition, the individual experiences physical symptoms including restlessness, alertness, and/or nervousness; being easily fatigued, difficulty concentrating or mind going blank, irritability, muscle tension, and sleep disturbance.

As used herein, the term "panic disorder" refers to a condition wherein an individual experiences recurrent and unexpected panic attacks. The individual is persistently concerned about having more panic attacks and changes his or her behavior in maladaptive ways because of these panic attacks, e.g. avoidance of exercise, unfamiliar locations, new people, etc.

As used herein, the term "panic attack" refers to an abrupt surge of intense fear or intense discomfort that reaches a peak within a short period of time, e.g., seconds, minutes, hours, etc. In some instances, a panic attack comprises a physical and/or cognitive symptom. Panic attacks may be predictable, such as in response to a typically feared object or situation. In some instances, a panic attack occurs for no apparent reason.

As used herein, the term "phobia" refers to a condition of being fearful, anxious about, or avoidant of a circumscribed object and/or situation. In some instances, a phobia comprises a fear, anxiety, or avoidance that is induced by a situation to a degree that is persistent and out of proportion to the actual risk posed. Examples of phobias include, but are not limited to, a fear or anxiety of an animal, a natural environment, an injection-injury, etc.

As used herein, the term "post traumatic stress disorder" refers to a condition developed after experiencing and/or witnessing a traumatic event or learning that a traumatic event has happened to a loved one. In some instances, a person shows symptoms of post traumatic stress disorder within a week of experiencing of the traumatic event. In some instances, a person shows symptoms of post traumatic stress disorder within a month of experiencing of the traumatic event. In some instances, a person shows symptoms of post traumatic stress disorder within a year of experiencing of the traumatic event. In some instances, a person shows symptoms of post traumatic stress disorder after a year or more of experiencing of the traumatic event. In some instances, post traumatic stress disorder comprises a person re-experiencing the trauma event through intrusive distressing recollections of the event, flashbacks, and/or nightmares. In some instances, a symptom of post traumatic stress disorder comprises emotional numbness and avoidance of places, people, and activities that are reminders of the trauma. In some instances, a symptom of post traumatic stress disorder comprises increased arousal such as difficulty sleeping and concentrating, feeling anxious, and being easily irritated and angered.

As used herein, the term "separation anxiety disorder" refers to a condition wherein an individual is fearful and/or anxious about separation from an attachment figure to a degree that is developmentally inappropriate. In some instances, a separation anxiety disorder comprises a fear or anxiety about harm coming to an attachment figure. In some instances, a separation anxiety disorder comprises a fear of an event leading to the loss of or separation from an attachment figure and reluctance to go away from attachment figures. In some instances, a separation anxiety disorder comprises a nightmare and/or psychical symptom of distress.

As used herein, the term "social anxiety disorder" refers to a condition wherein an individual is fearful, anxious about, or avoidant of social interactions and situations that involve the possibility of being scrutinized. These social interactions and situations include meeting unfamiliar people, situations in which the individual may be observed eating or drinking, situations in which the individual performs in front of others, etc. In some instances, a social anxiety disorder is caused by the fear of being negatively evaluated by others, by being embarrassed, humiliated, rejected, and/or offending others.

As used herein, the term "substance-induced anxiety disorder" refers to a condition wherein anxiety caused by a substance intoxication and/or a withdrawal or to a medical treatment. In some instances, a withdrawal from a substance increases anxiety.

As used herein, the term "selective mutism" refers to a condition characterized by an individual's consistent failure to speak in social situations in which there is an expectation to speak, e.g., school, a lecture, a meeting, etc., even though the individual speaks in other situations. Failure to speak has significant consequences on achievement in academics, occupational settings, and/or otherwise interferes with normal social communication.

In some instances, an anxiety disorder comprises a medical diagnosis based on the criteria and classification from the *Diagnostic and Statistical Manual of Medical Disorders, 5th Ed*. In some instances, an anxiety disorder comprises a medical diagnosis based on an independent medical evaluation. In some instances, an anxiety disorder comprises a medical diagnosis based on a self evaluation.

In one embodiment, the methods and compositions disclosed herein comprise administering an anxiolytic drug.

As used herein, the term "anxiolytic drug" refers to a compound or composition that reacts or influences activity at a neurotransmitter receptor, e.g., a serotonergic drug, an adrenergic receptor, a dopamine receptor, a GABAergic receptor, a glutaminergic receptor, a histaminergic receptor, a cholinergic receptor, an opioid receptor, or a glycinergic receptor, etc. In one embodiment, an anxiolytic drug binds on a neurotransmitter receptor. In one embodiment, an anxiolytic drug indirectly affects a neurotransmitter receptor, e.g., via interactions affecting the reactivity of other molecules at a neurotransmitter receptor. In one embodiment, an anxiolytic drug is an agonist. In one embodiment, an anxiolytic drug is an antagonist. In one embodiment, an anxiolytic drug acts (either directly or indirectly) at more than one type of a neurotransmitter receptor.

In one embodiment, an anxiolytic drug is chosen from alprazolam, an alpha blocker, an antihistamine, a barbiturate, a beta blocker, bromazepam, a carbamate, chlordiazepoxide, clonazepam, clorazepate, diazepam, flurazepam, lorazepam, an opioid, oxazepam, temazepam, or triazolam.

As used herein, the term "depressive disorder" refers to a condition of low mood and aversion to activity that can affect a person's thoughts, behavior, feelings, and sense of well-being lasting for a time period. In one embodiment, a depressive disorder disrupts the physical and psychological functions of a person. In one embodiment, a depressive disorder causes a physiological symptom, e.g., weight loss, aches or pains, headaches, cramps, digestive problems, etc. In one embodiment, a depressive disorder causes a psychological symptom, e.g., persistent sadness; anxiety; feelings of hopelessness and irritability; feelings of guilt, worthlessness, or helplessness; loss of interest or pleasure in hobbies and activities; difficulty concentrating, remembering, or making decisions, etc.

In one embodiment, a depressive disorder is chosen from atypical depression, bipolar disorder, catatonic depression, depressive disorder due to a medical condition, major depressive disorder, postpartum depression, premenstrual dysphoric disorder, or seasonal affective disorder.

As used herein, the term "atypical depression" refers to a condition wherein an individual shows signs of mood reactivity (i.e., mood brightens in response to actual or potential positive events), significant weight gain, increase in appetite, hypersomnia, heavy, leaden feelings in arms or legs, and/or long-standing pattern of interpersonal rejection sensitivity that results in significant social or occupational impairment. Exemplary symptoms of atypical depression include, but are not limited to, daily sadness or depressed mood; loss of enjoyment in things that were once pleasurable; major changes in weight (gain or loss) or appetite; insomnia or excessive sleep almost every day; a state of physical restlessness or being rundown that is noticeable by others; daily fatigue or loss of energy; feelings of hopelessness, worthlessness, or excessive guilt almost every day;

problems with concentration or making decisions almost every day; recurring thoughts of death or suicide, suicide plan, or suicide attempt.

As used herein, the term "bipolar disorder" refers to a condition that causes an individual to experience unusual shifts in mood, energy, activity levels, and the ability to carry out day-to-day tasks. Individuals with bipolar disorder experience periods of unusually intense emotion, changes in sleep patterns and activity levels, and unusual behaviors. These distinct periods are called "mood episodes." Mood episodes are drastically different from the moods and behaviors that are typical for the person. Exemplary symptoms of mania, excessive behavior, include, but are not limited to, abnormally upbeat, jumpy, or wired behavior; increased activity, energy, or agitation; exaggerated sense of well-being and self-confidence; decreased need for sleep; unusual talkativeness; racing thoughts; distractibility; and poor decision-making—for example, going on buying sprees, taking sexual risks, or making foolish investments. Exemplary symptoms of depressive episodes, low mood, include, but are not limited by, depressed mood, such as feelings of sadness, emptiness, hopelessness, or tearfulness; marked loss of interest or feeling no pleasure in all—or almost all—activities; significant weight loss, weight gain, or decrease or increase in appetite; insomnia or sleeping too much; restlessness or slowed behavior; fatigue or loss of energy; feelings of worthlessness or excessive or inappropriate guilt; decreased ability to think or concentrate, or indecisiveness; and thinking about, planning or attempting suicide.

As used herein, the term "catatonic depression" refers to a condition causing an individual to remain speechless and motionless for an extended period. Exemplary symptoms of catatonic depression include, but are not limited to, feelings of sadness, which can occur daily, a loss of interest in most activities, sudden weight gain or loss, a change in appetite, trouble falling asleep, trouble getting out of bed, feelings of restlessness, irritability, feelings of worthlessness, feelings of guilt, fatigue, difficulty concentrating, difficulty thinking, difficulty making decisions, thoughts of suicide or death, and/or a suicide attempt.

As used herein, the term "depressive disorder due to a medical condition" refers to a condition wherein an individual experiences depressive symptoms caused by another illness. Examples of medical conditions known to cause a depressive disorder include, but are not limited to, HIV/AIDS, diabetes, arthritis, strokes, brain disorders such as Parkinson's disease, Huntington's disease, multiple sclerosis, and Alzheimer's disease, metabolic conditions (e.g. vitamin B12 deficiency), autoimmune conditions (e.g., lupus and rheumatoid arthritis), viral or other infections (hepatitis, mononucleosis, herpes), back pain, and certain cancers (e.g., pancreatic).

As used herein, the term "major depressive disorder" refers to a condition characterized by a time period of low mood that is present across most situations. Major depressive disorder is often accompanied by low self-esteem, loss of interest in normally enjoyable activities, low energy, and pain without a clear cause. In some instances, major depressive order is characterized by two weeks. In some instances, an individual experiences periods of depression separated by years. In some instances, an individual experiences symptoms of depression that are nearly always present. Major depressive disorder can negatively affect a person's personal, work, or school life, as well as sleeping, eating habits, and general health. 2-7% of adults with major depressive disorder commit suicide, and up to 60% of people who commit suicide had major depressive disorder or another related mood disorder. Dysthymia is a subtype of major depressive disorder consisting of the same cognitive and physical problems as major depressive disorder with less severe but longer-lasting symptoms. Exemplary symptoms of a major depressive disorder include, but are not limited to, feelings of sadness, tearfulness, emptiness or hopelessness; angry outbursts, irritability or frustration, even over small matters; loss of interest or pleasure in most or all normal activities; sleep disturbances, including insomnia or sleeping too much; tiredness and lack of energy; reduced appetite, weight loss or gain; anxiety, agitation or restlessness; slowed thinking, speaking, or body movements; feelings of worthlessness or guilt, fixating on past failures or self-blame; trouble thinking, concentrating, making decisions, and remembering things; frequent thoughts of death, suicidal thoughts, suicide attempts, or suicide; and unexplained physical problems, such as back pain or headaches.

As used herein, the term "postpartum depression" refers to a condition as the result of childbirth and hormonal changes, psychological adjustment to parenthood, and/or fatigue. Postpartum depression is often associated with women, but men can also suffer from postpartum depression as well. Exemplary symptoms of postpartum depression include, but are not limited to, feelings of sadness, hopeless, emptiness, or overwhelmed; crying more often than usual or for no apparent reason; worrying or feeling overly anxious; feeling moody, irritable, or restless; oversleeping, or being unable to sleep even when the baby is asleep; having trouble concentrating, remembering details, and making decisions; experiencing anger or rage; losing interest in activities that are usually enjoyable; suffering from physical aches and pains, including frequent headaches, stomach problems, and muscle pain; eating too little or too much; withdrawing from or avoiding friends and family; having trouble bonding or forming an emotional attachment with the baby; persistently doubting his or ability to care for the baby; and thinking about harming themselves or the baby.

As used herein, the term "premenstrual dysphoric disorder" refers to a condition wherein an individual expresses mood lability, irritability, dysphoria, and anxiety symptoms that occur repeatedly during the premenstrual phase of the cycle and remit around the onset of menses or shortly thereafter. Exemplary symptoms of premenstrual dysphoric disorder includes, but are not limited to, lability (e.g., mood swings), irritability or anger, depressed mood, anxiety and tension, decreased interest in usual activities, difficulty in concentration, lethargy and lack of energy, change in appetite (e.g., overeating or specific food cravings), hypersomnia or insomnia, feeling overwhelmed or out of control, physical symptoms (e.g., breast tenderness or swelling, joint or muscle pain, a sensation of 'bloating' and weight gain), self-deprecating thoughts, feelings of being keyed up or on edge, decreased interest in usual activities (e.g., work, school, friends, hobbies), subjective difficulty in concentration, and easy fatigability.

As used herein, the term "seasonal affective disorder" refers to a condition wherein an individual experiences mood changes based on the time of the year. In some instances, an individual experiences low mood, low energy, or other depressive symptoms during the fall and/or winter season. In some instances, an individual experiences low mood, low energy, or other depressive symptoms during the spring and/or summer season. Exemplary symptoms of seasonal affective disorder include, but are not limited to, feeling depressed most of the day or nearly every day; losing interest in activities once found enjoyable; having low energy; having problems with sleeping; experiencing changes in appetite or weight; feeling sluggish or agitated; having difficulty concentrating; feeling hopeless, worthless, or guilty; and having frequent thoughts of death or suicide.

In one embodiment, a depressive disorder comprises a medical diagnosis based on the criteria and classification from Diagnostic and Statistical Manual of Medical Disorders, 5th Ed. In one embodiment, a depressive disorder comprises a medical diagnosis based on an independent medical evaluation.

In one embodiment, the methods and compositions disclosed herein comprise administering an antidepressant.

As used herein, the term "antidepressant" refers to a compound or compounds that reacts or influences activity at a neurotransmitter receptor, e.g., a serotonergic drug, an adrenergic receptor, a dopamine receptor, a GABAergic receptor, a glutaminergic receptor, a histaminergic receptor, a cholinergic receptor, an opioid receptor, or a glycinergic receptor, etc. In one embodiment, an antidepressant binds on a neurotransmitter receptor. In one embodiment, an antidepressant indirectly affects a neurotransmitter receptor, e.g., via interactions affecting the reactivity of other molecules at a neurotransmitter receptor. In one embodiment, an antidepressant is an agonist. In one embodiment, an antidepressant is an antagonist. In one embodiment, an antidepressant acts (either directly or indirectly) at more than one type of neurotransmitter receptor.

In one embodiment, an antidepressant is chosen from buproprion, citalopram, duloxetine, escitalopram, fluoxetine, fluvoxamine, milnacipran, mirtazapine, paroxetine, reboxetine, sertraline, and venlafaxine.

Disclosed herein is a method of treating headaches and/or migraines, comprising identifying a person in need of treatment and administering a composition disclosed herein to the person in need of treatment.

Disclosed herein is a method of treating nicotine addiction, comprising identifying a person in need of treatment and administering a composition disclosed herein to the person in need of treatment.

Disclosed herein is a method of treating drug addiction, comprising identifying a person in need of treatment and administering a composition disclosed herein to the person in need of treatment.

Disclosed herein is a method of treating alcohol addiction, comprising identifying a person in need of treatment and administering a composition disclosed herein to the person in need of treatment.

The compositions disclosed herein are useful for the treatment of compulsive disorders in humans, a variety of intractable psychiatric disorders, chronic depression, post-traumatic stress disorder, and drug or alcohol dependency. The compositions disclosed herein are also useful within the context of meditative, spiritual, and religious practices within a variety of contexts.

As used herein, the term "compulsive disorder" refers to a condition wherein an individual has an obsession causing a feeling of anxiety, fear, apprehension, etc., and has a compulsion to perform tasks to relieve said feeling of anxiety. An obsession is a thought that recurs and persists despite efforts of an individual to ignore or confront them. In some instances, an obsession is relatively vague involving a general sense of disarray or tension accompanied by a belief that life cannot proceed as normal while the imbalance remains. In other instances, an obsession is more intense and could be a preoccupation with the thought or image of someone close to them dying or intrusions related to relationship rightness. Other obsessions concern the possibility that someone or something other than oneself—such as God, the Devil, or disease—will harm either the person, the people or things that the person cares about. In some instances, individuals perform compulsive rituals because they inexplicably feel they have to. In some instances, individuals perform compulsive rituals to mitigate the anxiety that stems from a particular obsession. The person feels that these actions will somehow either prevent a dreaded event from occurring or will push the event from their thoughts.

In one embodiment, a compulsive disorder is chosen from addiction, body dysmorphic disorder, excoriation disorder, hoarding disorder, obsessive compulsive disorder, and trichotillomania.

As used herein, the term "addiction" refers to a physical and/or psychological dependence on a substance, activity, and/or any other habit. In one embodiment, an addiction is caused by the altered brain chemistry of an individual in response to a stimulus, e.g., a substance releasing large amounts of serotonin, an activity releasing large amounts of adrenaline, etc. In one embodiment, an addiction is a dependence on a substance, e.g., a drug, an alcohol, nicotine, a food, etc. In one embodiment, an addiction is a dependence on an activity, e.g., gambling, eating, shopping, etc.

As used herein, the term "body dysmorphic disorder" refers to a condition characterized by the obsessive idea that some aspect of an individual's appearance is severely flawed and warrants exceptional measures to hide or fix it. Exemplary symptoms of body dysmorphic disorder includes, but are not limited to, being extremely preoccupied with a perceived flaw in appearance that to others can't be seen or appears minor; a belief that a defect in appearance makes an individual ugly or deformed; a belief that others take special notice of an individual's appearance in a negative way or mock the individual; engaging in behaviors aimed at fixing or hiding the perceived flaw that are difficult to resist or control, such as frequently checking the mirror, grooming, or skin picking; attempting to hide perceived flaws with styling, makeup, or clothes; constantly comparing one's appearance with others; always seeking reassurance about one's appearance from others; having perfectionist tendencies; seeking frequent cosmetic procedures with little satisfaction; avoiding social situations; and being so preoccupied with one's appearance that it causes major distress or problems in the person's social life, work, school, or other areas of functioning.

As used herein, the term "excoriation disorder" refers to a condition of having a repeated urge to pick at one's own skin. In some instances, an excoriation disorder causes a person to often to pick their skin to the extent that damage is caused.

As used herein, the term "hoarding disorder" refers to a condition of persistent difficulty in discarding or parting with possessions, regardless of their value. Exemplary symptoms of a hoarding disorder include, but are not limited to, inability to throw away possessions; severe anxiety when attempting to discard items; great difficulty categorizing or organizing possessions; indecision about what to keep or where to put things; distress, such as feeling overwhelmed or embarrassed by possessions; suspicion of other people touching items; obsessive thoughts and actions; fear of running out of an item or of needing it in the future; checking the trash for accidentally discarded objects; and functional impairments, e.g., loss of living space, social isolation, family or marital discord, financial difficulties, health hazards, etc.

As used herein, the term "obsessive compulsive disorder" refers to a condition in which an individual has uncontrollable, reoccurring thoughts and behaviors that he or she feels the urge to repeat over and over. In some instances, an obsessive-compulsive disorder manifests itself as an individual needing to clean in order to reduce the fear that germs, dirt, or chemicals will contaminate the individual and the individual will spend many hours washing themselves or cleaning their surroundings. In some instances, an obsessive-compulsive disorder manifests itself as an individual needing to dispel anxiety. An individual may utter a name, phrase or repeat a behavior several times. The individual knows these repetitions will not actually prevent injury, but fear of harm will occur if the repetitions are not performed. In some instances, an obsessive-compulsive disorder manifests itself as an individual needing to reduce the fear of harming oneself or by others by, e.g., forgetting to lock the door or turning off appliances, developing checking rituals, etc. In some instances, an obsessive-compulsive disorder manifests itself as an individual needing to order and arrange his or her surroundings to reduce discomfort, e.g., putting objects in a certain order, arranging household items in a particular manner or in a symmetric fashion, etc. In some instances, an obsessive-compulsive disorder manifests itself as an individual needing to respond to intrusive obsessive thoughts, e.g., praying or saying phrases to reduce anxiety or prevent a dreaded future event. In some instances, obsessive compulsive disorder is caused by another medical condition. In some instances, obsessive compulsive disorder is caused by a substance.

As used herein, the term "trichotillomania" refers to a condition of self-induced and recurrent loss of hair, e.g., pulling one's own hair out. In some instances, trichotillomania comprises an individual pulling their hair out at one location. In some instances, trichotillomania comprises an individual pulling their hair out at multiple locations. Exemplary symptoms of trichotillomania include, but are not limited to, recurrent pulling out of one's hair resulting in noticeable hair loss; an increased sense of tension immediately before pulling out the hair or when resisting the behavior; pleasure, gratification, or relief when pulling out the hair; the disturbance is not accounted for by another mental disorder and is not due to a general medical condition (i.e., dermatological condition); repeated attempts have been made to decrease or stop hair pulling; disturbances caused significant distress or impairment in social, occupational, or other important areas of functioning; distress including feelings of loss of control, embarrassment, shame; and impairment due to avoidance of work, school, or other public situations.

In one embodiment, a compulsive disorder comprises a medical diagnosis based on the criteria and classification from Diagnostic and Statistical Manual of Medical Disorders, 5th Ed. In one embodiment, a compulsive disorder comprises a medical diagnosis based on an independent medical evaluation.

Disclosed herein are formulations comprising a composition disclosed herein and at least one compound not acting on serotonin receptors.

Although the disclosed invention has been described with reference to various exemplary embodiments, it is to be understood that these embodiments are merely illustrative of the principles and applications of the present invention. Those having skill in the art would recognize that various modifications to the exemplary embodiments may be made, without departing from the scope of the invention.

Where reference is made to a particular compound, it should be understood that this disclosure also contemplates salts and derivatives of that compound as well as degradation products, such as oxidized versions of explicitly disclosed molecules.

Moreover, it should be understood that various features and/or characteristics of differing embodiments herein may be combined with one another. It is therefore to be understood that numerous modifications may be made to the illustrative embodiments and that other arrangements may be devised without departing from the scope of the invention.

Furthermore, other embodiments of the invention will be apparent to those skilled in the art from consideration of the specification and practice of the invention disclosed herein. It is intended that the specification and examples be considered as exemplary only, with a scope and spirit being indicated by the claims.

Finally, it is noted that, as used in this specification and the appended claims, the singular forms "a," "an," and "the," include plural referents unless expressly and unequivocally limited to one referent, and vice versa. As used herein, the term "include" or "comprising" and its grammatical variants are intended to be non-limiting, such that recitation of an item or items is not to the exclusion of other like items that can be substituted or added to the recited item(s).

What is claimed is:

1. A method of treating a psychological disorder comprising administering a dosage composition comprising a homogenous mixture of a first serotonergic drug and a purified psilocybin derivative selected from the group consisting of 3-(2-dimethylaminoethyl)-1H-indol-4-yl]dihydrogen phosphate, 4-hydroxy-N,N-dimethyltryptamine, [3-(2-trimethylaminoethyl)-1H-indol-4-yl]dihydrogen phosphate, 4-hydroxy-N,N,N-trimethyltryptamine, [3-(2-methylaminoethyl)-1H-indol-4-yl]dihydrogen phosphate, 4-hydroxy-N-methyltryptamine, [3-(aminoethyl)-1H-indol-4-yl] dihydrogen phosphate, 4-hydroxytryptamine, and their salts to a subject in need thereof.

2. The method of claim 1, wherein the first serotonergic drug comprises a Selective Serotonin Reuptake Inhibitor.

3. The method of claim 2, wherein the Selective Serotonin Reuptake Inhibitor is 90-100% pure.

4. The method of claim 3, wherein the Selective Serotonin Reuptake Inhibitor comprises escitalopram.

5. The method of claim 1, wherein the purified psilocybin derivative is 3-(2-Dimethylaminoethyl)-1H-indol-4-yl]dihydrogen phosphate.

6. The method of claim 1, wherein the purified psilocybin derivative is 4-hydroxy-N,N-dimethyltryptamine.

7. The method of claim 1, wherein the dosage composition further comprises an excipient.

8. The method of claim 1, wherein the first serotonerigic drug or the purified psilocybin derivative is in the form of a dried powder.

9. The method of claim 8, wherein the purified psilocybin derivative is in crystalline form.

10. The method of claim 1, wherein the purified psilocybin derivative is 90-100% pure.

11. The method of claim 8, wherein the first serotonergic drug is a Selective Serotonin Reuptake Inhibitor in crystalline form.

12. The method of claim 1, wherein the psychological disorder is chosen from an anxiety disorder, a compulsive disorder, addiction, and a depressive disorder.

* * * * *